United States Patent [19]

Miyoshi et al.

[11] 4,354,602

[45] Oct. 19, 1982

[54] DEVICE FOR INSPECTING THE EXTERNAL APPEARANCE OF SOLID MEDICINE

[75] Inventors: Noriomi Miyoshi; Yoshio Sugiyama; Tetsuji Kawasaki, all of Kawasaki; Jun Yamaguchi, Hiro; Kouji Shiino, Hiro; Mamoru Shiratori, Hiro, all of Japan

[73] Assignees: Fuji Electric Co., Ltd., Kawasaki; Sankyo Company, Limited, Tokyo, both of Japan

[21] Appl. No.: 22,004

[22] Filed: Mar. 19, 1979

[30] Foreign Application Priority Data

Mar. 17, 1978 [JP] Japan .................................. 53-30821
Aug. 7, 1978 [JP] Japan .................................. 53-96007

[51] Int. Cl.$^3$ ............................................. B07C 5/342
[52] U.S. Cl. .................................... 209/545; 209/577; 209/586; 209/701; 209/919; 250/223 R; 474/156
[58] Field of Search .............. 209/540, 545, 576, 577, 209/580, 581, 586, 701, 905, 919; 250/223 R; 474/156

[56] References Cited

U.S. PATENT DOCUMENTS

| | | | |
|---|---|---|---|
| 3,097,743 | 7/1963 | Scholten et al. ................. | 209/905 X |
| 3,490,303 | 1/1970 | Rosenberg .......................... | 474/156 |
| 3,757,943 | 9/1973 | Chae et al. ....................... | 209/701 X |
| 3,969,227 | 7/1976 | Garris ............................. | 209/905 X |
| 4,082,188 | 4/1978 | Grimmell et al. ................... | 209/580 |

*Primary Examiner*—Joseph J. Rolla

*Attorney, Agent, or Firm*—Sughrue, Rothwell, Mion, Zinn and Macpeak

[57] ABSTRACT

A device for inspecting the external appearance of solid medicine having a solid medicine supplying section, a first drum-shaped conveying section for conveying solid medicines supplied by the solid medicine supplying section, at equal intervals so that one surface of each piece of solid medicine is observed. A second drum-shaped conveying section receives the solid medicine from the first drum-shaped conveying section and conveys the solid medicine at equal intervals so that the opposite surface of each solid medicine is observed. First and second observing units are provided adjacent to said first and second drum-shaped conveying sections for observing both surfaces of each piece of solid medicine respectively. A third observing unit is employed for observing the thickness of each piece of solid medicine conveyed by the first and second drum-shaped conveying sections at least before the piece of solid medicine reaches the second observing unit. A discriminating circuit determines whether each piece of solid medicine is acceptable or unacceptable according to observation results provided by the first, second and third observing units and a memory stores every solid medicine discrimination signal outputted on the basis of the observation results provided by the first and third observing units. The discrimination signal based on the observation result provided by the second observing unit and the discrimination signals stored in said memory are utilized for general determination as to whether the external appearance of each piece of solid medicine is acceptable or unacceptable.

22 Claims, 33 Drawing Figures

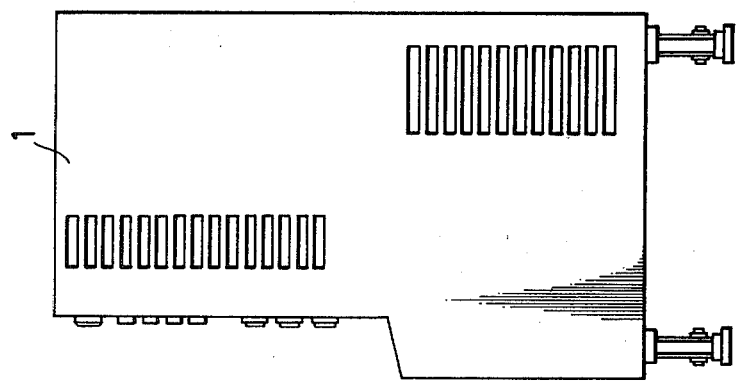
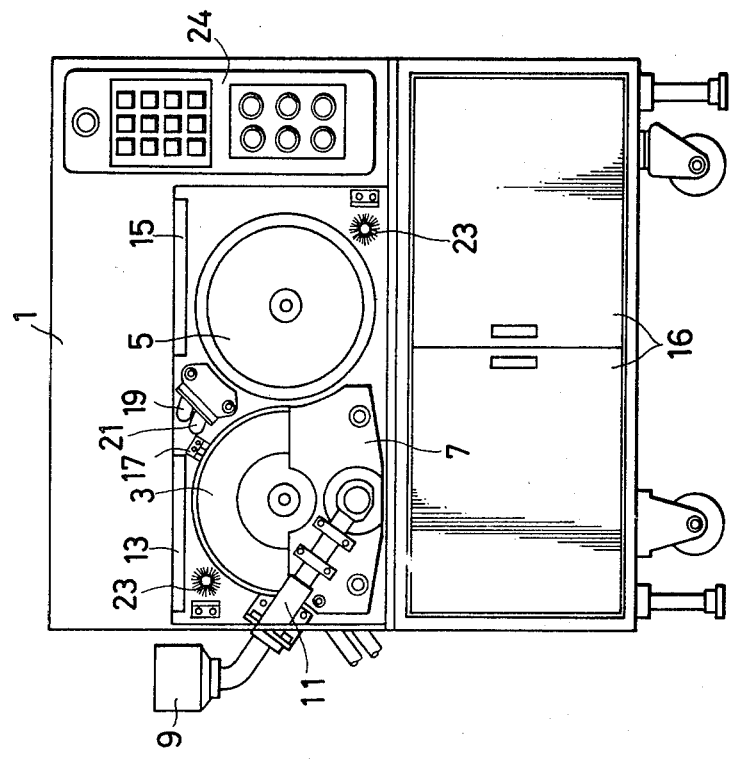

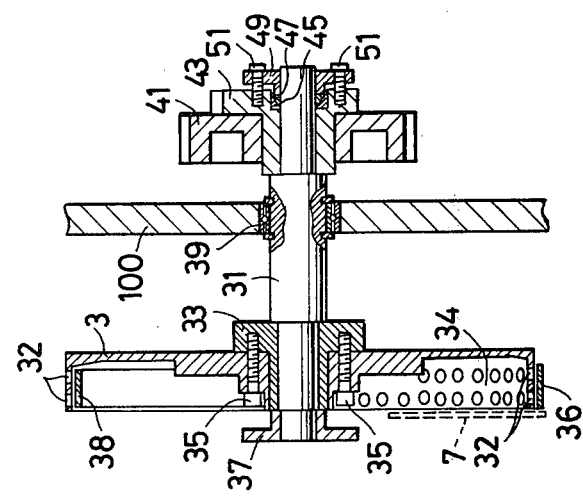

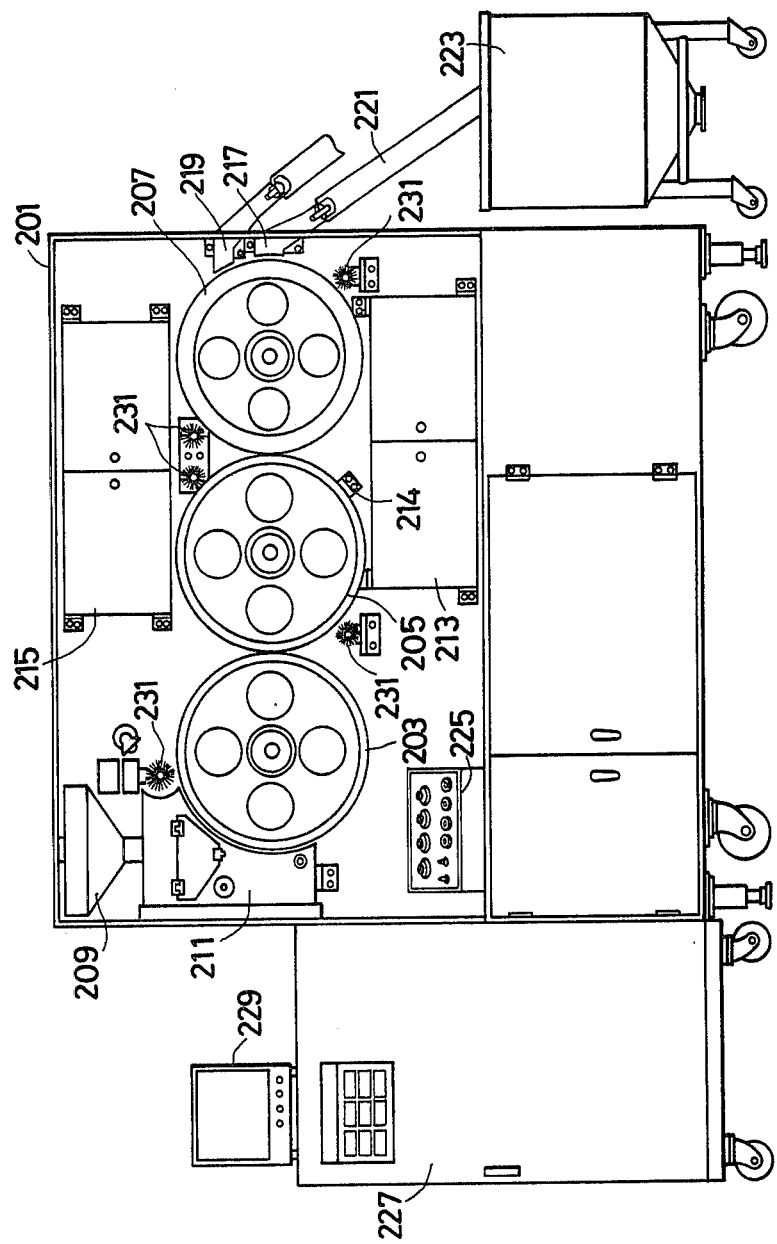

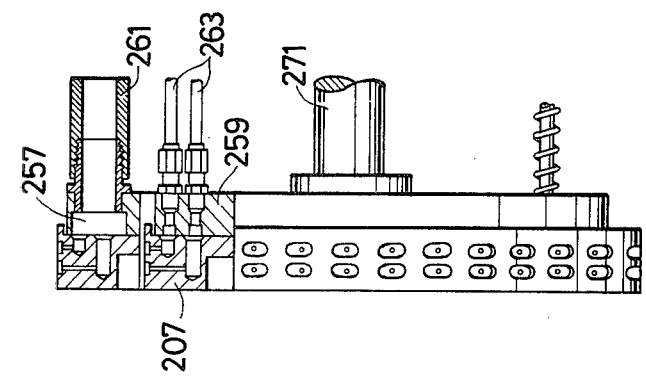
FIG. 13D  FIG. 13C  FIG. 13B
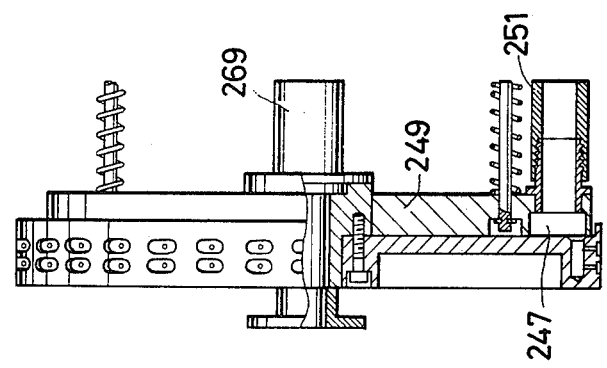
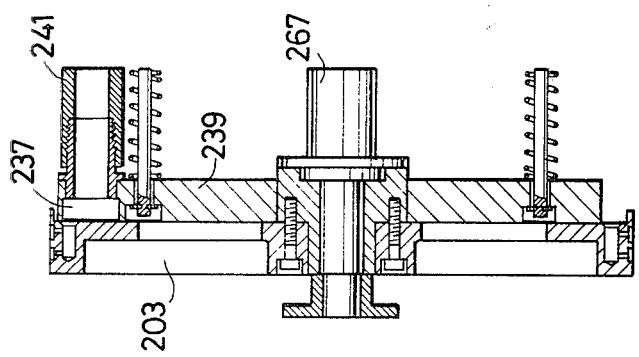

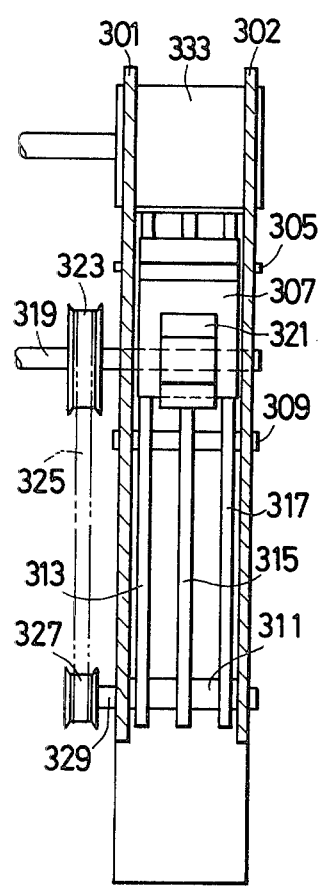
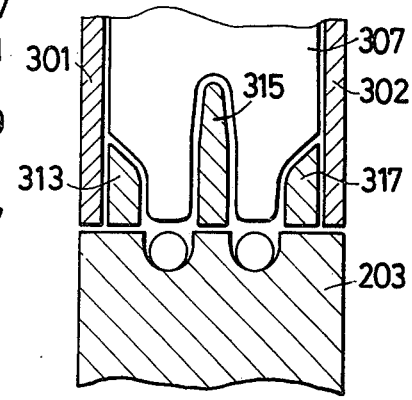
FIG. 14B
FIG. 14C

DEVICE FOR INSPECTING THE EXTERNAL APPEARANCE OF SOLID MEDICINE

BACKGROUND OF THE INVENTION

This invention relates to a device for inspecting the external appearance of medicine such as a tablet, a capsule, a pellet or other objects (hereinafter referred to as "solid medicine") to determine whether it is acceptable or not.

Heretofore, the external appearance of such solid medicine has only been visually inspected. However, this technique suffers from problems in that the classifying capability is lowered because of fatigue, and the classification standard fluctuates because of the differences in human selection criteria. Furthermore, in association with increasing personnel expenses and the requirement for increasing the inspection speed, there has been a strong demand for mechanically carrying out this inspection.

In carrying out the external appearance inspection of solid medicine by the use of a mechanical means, the mechanical system should satisfy the following conditions:

(a) Solid medicine is automatically and smoothly supplied;

(b) At least one surface of a piece of solid medicine and the opposite surface (in the case of a capsule, the upper half surface and the lower half surface thereof when laid) are automatically observed;

(c) Even in the case where one surface of a piece of solid medicine is different in external appearance from the opposite surface (for instance in the case where only one of the two surfaces of a solid medicine has marks, or in the case where the color of one surface is different from that of the opposite surface), the external appearance thereof can be positively inspected; and (d) The device is simply constructed and the maintenance and inspection thereof can be readily achieved.

If the piece of solid medicine is small, it is, in general, difficult to simultaneously observe both surfaces thereof to meet the requirement (b). In this case, after one surface thereof has been observed, it is necessary to use a paticular device to turn over the piece to observe the opposite surface. In this connection and in view of requirement (c), a device which may give mechanical vibration or impact to the solid medicine cannot be utilized as the solid medicine turning over means. Stated differently, the results of observation of two surfaces of solid medicine must be combined in the general determination. Therefore, there should be no possibility that when solid medicine is turned over, it interchanges place with another, or it is transposed to a position where no solid medicine has been placed.

Conventional external appearance inspecting devices of this type have been investigated from the above-described criteria, however, no device satisfying the conditions (a) through (d) fully has not been proposed or has reached the point of commercial acceptance.

SUMMARY OF THE INVENTION

Accordingly, an object of this invention is to provide an external appearance inspecting device which meets all of the above-described conditions (a) through (d) and smoothly turns over pieces of solid medicine, so that the external appearance is correctly and automatically inspected.

It is another object of this invention to provide a system for inspecting the appearance of medicine that operates at a speed making it cost efficient and compatible with production speeds.

A further object of this invention is to provide a system for inspecting the appearance of medicine that accurately examines the appearance of each piece passing for inspection.

In order to achieve these objects, a fundamental feature of the invention resides in the use two adjacent drum-shaped conveying sections as a mechanism for turning over solid medicine. Two such adjacent drum-shaped conveying sections have been employed for turning over solid medicine, for instance, in a machine operating to print symbols or trade names on solid medicine. However, all that is required for this machine is to turn over the pieces of solid medicine; that is the correspondence of 1:1 between the two surfaces of each solid medicine in inspection as described above is not required for such an operation. Accordingly, it is obvious that the aforementioned objects cannot be achieved merely by replacing the printing mechanism of the machine by observing mechanisms.

Thus, in this invention, a discrimination signal for determining whether solid medicine is acceptable or not, is provided on the result of observation of one surface thereof. This signal is stored in a memory device such as a shift register and this discrimination signal together with another discrimination signal based on the result of an observation of the opposite surface are combined to collectively determine the acceptability of the piece of solid medicine. The shift register of the memory device should be such that its bit number is equal to the number of pieces of solid medicine existing between one observing unit and another observing unit. If, in this connection, the discrimination signal per surface of each piece of solid medicine is of a plurality of bits, a corresponding parallel bit number shift register may be employed. Furthermore, in the case where a plurality of pieces of solid medicine are to be inspected simultaneously, the number of shift registers may be increased according to the number of pieces of solid medicine to be inspected simultaneously. Naturally an ordinary random access memory may be employed as the memory device to process the inspection in a software mode.

In a preferred embodiment of the invention, a drum-shaped conveying section used only for supplying solid medicine is provided to satisfy the above-described conditions (a) through (d). This three-drum system is very effective when put in practical use.

The arrangements, operations and effects of embodiments of this invention will be described with reference to the accompanying drawings.

BRIEF DESCRIPTION OF THE DRAWINGS

FIGS. 1A and 1B are a front view and a side view showing one example of an external appearance inspecting device in accordance with a two-drum system, embodying this invention, respectively;

FIGS. 2B and 2C are sectional views taken along line B—B and C—C in FIG. 2, respectively;

FIGS. 12A and 12B are a front view and a side view showing a third example of the device according to the invention, the device being operated in accordance with a three-drum outside supply system;

FIGS. 13B, 13C and 13D show sectional views taken along lines F—F, G—G and H—H in FIG. 13A, respectively;

FIGS. 14A, 14B and 14C describe a container 211 shown in FIG. 12A, more specifically, FIGS. 14A and 14B are a front view and a side view showing the container, and FIG. 14C is a sectional view taken along line J—J in FIG. 14A;

DETAILED DESCRIPTION OF THE PREFERRED EMBODIMENTS

Figure 2A:
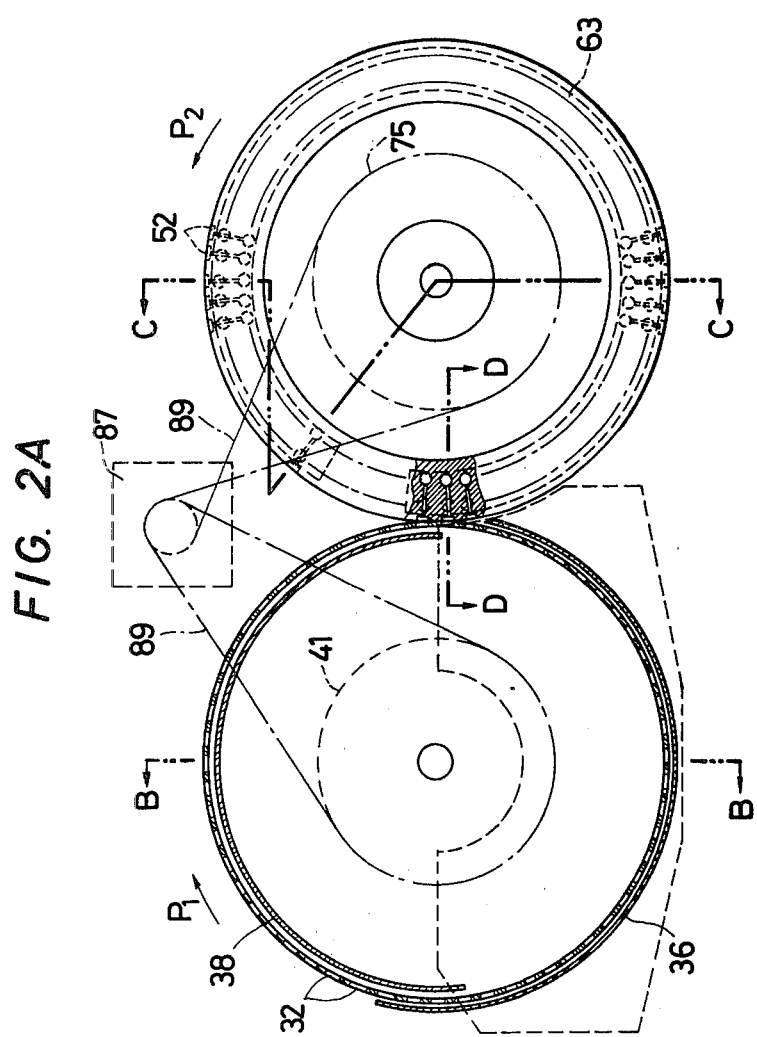
FIG. 2A is an enlarged view of the essential components of a first drum and a second drum in the two-drum system.

FIGS. 1A and 1B show the external appearance inspecting device employing a two-drum inside supply system in which two drum-shaped conveying sections are provided adjacent to each other as a solid medicine turning over mechanism. The solid medicine pieces are supplied into the inside of one of the drum-shaped conveying sections. The arrangement of this device is generally as stated below:

In FIGS. 1A and 1B, reference numeral 1 designates a housing. This housing has a solid medicine supplying section, a first drum-shaped conveying section 3 (hereinafter referred to as "a first drum 3" when applicable) for inspecting one surface of a solid medicine with a first observing unit 13, and a second drum-shaped conveying section 5 (hereinafter referred to as "a second drum 5" when applicable) for receiving solid medicine pieces from the first drum and inspecting the other surface thereof with a second observing unit 15. A side plate 7 is provided adjacent to the first drum 3.

Solid medicine pieces are delivered into the first drum 3 from a hopper through a chute 11 coupled to the side plate 7, to a predetermined amount, and are stored therein. The pieces of solid medicine are inspected by the first observing unit 13 and the second observing unit 15 while being transferred from the first drum 3 to the second drum 5. The solid medicine pieces thus inspected are further subjected to inspection by an acceptability determining device provided inside a pair of doors 16 to determine whether or not the external appearance of each piece of solid medicine is acceptable. According to that determination, the acceptable pieces and the unacceptable pieces are delivered out through an acceptable transferring pipe 19 and an unacceptable transferring pipe 21, respectively. Cleaner brushes 23 are provided adjacent to the outer circumferential surfaces of the first drum 3 and the second drum 5, respectively. A display and operating panel 24 are provided on the front wall of the housing 1.

The first drum 3 is made up of a hollow cylindrical container which, as shown in FIGS. 2A and 2B, has through-holes 32 provided at equal intervals circumferentially of the container. The first drum 3 is fitted over a bushing 33 fixedly mounted on a drum shaft 31 and is fixedly secured thereto with screws 35. A depressing member 37 is mounted on the drum shaft 31. The drum shaft 31 is supported through a bearing 39 by a base plate 100. A pulley 41 is provided at one end portion of the drum shaft 31 opposite the end portion where the drum is provided. The pulley 41 is fixed to an adjusting metal fitting 43, which is tightened to a depressing member 49 adapted to depress a shaft fixing metal fitting comprising a retaining ring 45 and a depressing ring 47 with screws 51.

Similar to the first drum 3, the second drum 5 is made up of a disk which, as shown in FIGS. 2A and 2C, has a plurality of holes 52 provided at equal intervals circumferentially of the disk. The second drum 5 is secured to a bushing 55 with screws 53. A slide plate 57 is provided in such a manner that it surrounds the bushing 55 and is in close contact with the drum. The slide plate 57 is in the form of a disk and is supported on a base plate 100 by means of a supporting rods 59. The supporting rods 59 are provided with springs 61 adapted to depress the slide plate 57 toward the second drum 5. The slide plate 57 has a vacuum chamber 63 at the position where the slide plate 57 is in contact with the second drum 5.

The vacuum chamber 63 is in the form of an arc as indicated by the dotted line in FIG. 2A. The vacuum chamber 63 is connected through connecting metal fittings 65 to suction pipes 67. The vacuum chamber 63 is communicated with the holes 52 of the second drum 5 through vacuum suction ports 54. Discharging jet nozzles 69 are secured to the slide plate 57 so that jet air flows are applied separately to the holes 52 of the second drum 5. A drum shaft 73 is supported on the base plate 100 through a bearing 71.

A pulley 75 is secured to the drum shaft 73 by means of an adjusting metal fitting 77. This adjusting metal fitting is tightened to a depressing member 83 adapted to depress a shaft fixing metal fitting comprising a fixing ring 79 and a depressing ring 81 with screws 85.

The first drum 3 and the second drum 5 are rotated in the opposite directions by a driving mechanism which as shown in FIG. 2A. It comprises an electric motor 87, and toothed belts laid over the motor 87 and the pulleys 41 and 75. That is, the first drum 3 is rotated in the direction of the arrow P1, and the second drum 5 is rotated in the direction of the arrow P2.

The side plate provided adjacent to the first drum 3 and the hollow section of the first drum 3 form a chamber 34. A predetermined number of pieces of solid medicine 30 are delivered into the chamber 34 through the chute 11 from the hopper 9 shown in FIG. 1A and are stored therein. An outside guide 36 and an inside guide 38 are provided outside and inside the first drum 3, respectively. The outside guide 36 and the inside guide 38 serve to prevent the solid medicine 30 from dropping through the through-holes 32 of the first drum 3. The solid medicine pieces 30 stored in the chamber 34 of the first drum 3 are inserted in the through-holes 32 respectively and are moved upward while being retained by the outside and inside guide plates 36 and 38 as the drum is rotated.

When each piece of solid medicine in the respective through-hole 32 conveyed upward by the rotation of the drum 3, reaches the top of the drum one surface of the piece is inspected by the first observing unit 13 provided above the drum as shown in FIG. 1A. An industrial television camera is most suitable as the observing unit 13, or the observing unit 15 described later. The inspection done by the observing unit will be described with reference to applicable figures later. The solid medicine piece passing through the position of the first observing unit 13 then reaches a third observing unit, namely, a sensor 17. This sensor 17 operates to inspect data which cannot be inspected by the first observing unit 13, for instance the thickness or the posture of a piece of solid medicine. In the case when an abnormality in the thickness or posture of solid medicine pieces which may cause a so-called "jamming" is detected by the sensor 17, it is necessary to automatically discharge the unacceptable pieces to thereby prevent an occurrence of "jamming". It is thus desirable that a well known means utilizing a jet air flow for instance, which operates to achieve the discharge operation in response to the detection signal of sensor 17, is provided just behind the sensor 17.

Figure 3A:
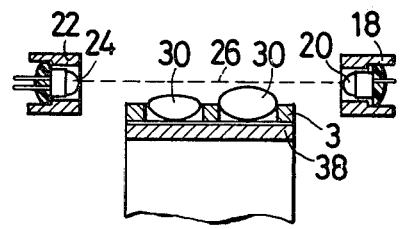
FIGS. 3A and 3B are a sectional view and a plan view showing the arrangement of a sensor 17.
Figure 3B:
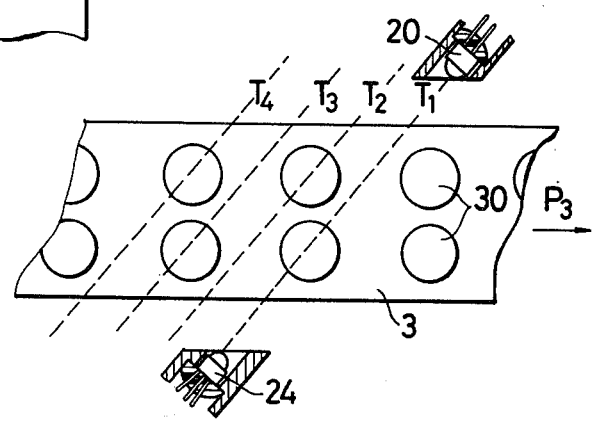

The arrangement of the sensor 17 is as shown in FIGS. 3A and 3B. More specifically, a light emitting unit 20 in a holder 18, and a photoelectric converter 24 in a holder 22 are disposed on the optical axis 26 (indicated by the dotted line) in such a manner that they confront each other along the outer wall of the first drum 3. Furthermore, if it is assumed that the solid medicine pieces 30 are conveyed in two lines as shown in FIG. 3B, the optical axis of the light emitting unit 20 and the photoelectric converter 24 forms an angle $\theta$ with respect to the direction of advancement of the pieces of solid medicine 30. The optical axis is indicated by the dotted line also in FIG. 3B.

In the case where the optical axis 26 shown in FIG. 3A is employed as a reference, if, for instance, a piece 30 is recessed, then the amount of interception of light applied from the light emitting unit 20 to the photoelectric converter 24 is decreased to an extent, and therefore the output of the photoelectric converter 24 is increased. If a piece of solid medicine is enlarged, then the amount of interception of light is increased and therefore the output of the photoelectric converter 24 is decreased. Since the light emitting unit 20 and the photoelectric converter 24 are disposed so that the optical axis forms the angle $\theta$ with the direction of movement of the solid medicine pieces as shown in FIG. 3B, only one sensor is needed to inspect the thickness of pieces of solid medicine moving in two lines.

In practice, the first drum 3 is moved in the direction of the arrow P3, and the sensor is stationary. However, for convenience in description, the drum 3 is stationary, and the sensor is moved in FIG. 3B. As is apparent from the optical axes T1, T2, T3 and T4 representing the movement of the sensor, the pieces 30 in two lines are alternately inspected. In the case of FIG. 3B, the solid medicine 30 is in two lines; however, in the case also where the solid medicine 30 is in more than two lines, they can be effectively inspected by inclining the optical axis of the light emitting unit 20 and the photoelectric coverter 24. The electrical arrangement of the sensor 17 will be described in more detail latter with reference to the applicable figures.

When a piece of solid medicine passing through the first observing unit 13 and the sensor 17 shown in FIG. 1A reaches the position where the first drum 3 is brought into contact with the second drum 5, it is transferred into the second drum 5 from the first drum 3. Since the holes 52 in the circumferential wall of the second drum 5 are evacuated by the vacuum chamber 63 provided at the position where the second drum 5 is in contact with the slide plate 57, the piece placed in the through-hole 32 of the first drum 3 is transferred into the hole 52 of the second drum 5.

In this connection, it is necessary that the through-holes 32 of the first drum 3 coincide with the holes 52 of the second drum 5 at the position where the first drum 3 is brought into contact with the second drum 5. This requirement can be satisfied by increasing the machine accuracy. If there is the possibility that the rotations of the two drums may become out of phase during a long run, the phase difference can be corrected by adjusting the positions of the drums during the periodic inspection or by the provision of an automatic phasing mechanism. The latter is well known in the art, for example, register control technique of a rotary press.

When the piece of solid medicine is transferred from the first drum 3 to the second drum 5, one surface of the piece which appeared in the hole of the first drum will now confront with the bottom of the hole 52 of the second drum 5. That is, the piece of solid medicine is moved by the second drum 5 while exposing the opposite surface thereof. When the piece is brought to the top position of the drum as the drum is rotated, the opposite surface is inspected by the second observing unit 15. After the surface is inspected by the second observing unit 15, the external appearance is further subjected to general inspection by the general acceptability determining device (described later) according to the inspection result of the first observing unit 13 or the inspection result of the sensor 17 as the case may be.

After passing through the position of the second observing unit 15, the piece is moved to the position of the acceptable transferring pipe 19. As is apparent from FIGS. 2A and 2C, the holes 52 of the second drum 5 confronting with the pipe 19 communicate with the discharging jet nozzles 69 and 69, respectively. Therefore, the pieces in the holes 52 of the second drum 5 are individually discharged by the jet air flows from the discharging jet nozzles. In FIGS. 2A and 2C, the discharging jet nozzles 69 confront with the acceptable transferring pipe 19. Similar to nozzles 69, discharging jet nozzles for discharging unacceptable pieces of solid medicine into the unacceptable transferring pipe 21 are provided for the second drum 5. The jet air flows from the discharging jet nozzles can be obtained by operating electromagnetic valves, connected thereto, according to the general determination based on the inspection results provided by the first observing unit 13 and the second observing unit 15. The solid medicine pieces transferred into the pipes 19 and 21 are selectively conveyed into an acceptable tank and an unacceptable tank, respectively.

When the piece is transferred from the first drum 3 to the second drum 5, the through-holes 32 of the first drum 3 must coincide with the holes 52 of the second drum 5 at the position where the two drums are brought into contact with each other. For this purpose, drum fine adjustment mechanisms for adjusting the positions of the drums are provided. The mechanisms correspond to the mechanism including the pulley 41 and the mechanism including the pulley 75 in FIGS. 2B and 2C. One of the drum fine adjustment mechanisms will be described with reference to FIGS. 4A and 4B which are enlarged diagrams showing the pulley 75 and its concerning components.

Figure 4A:
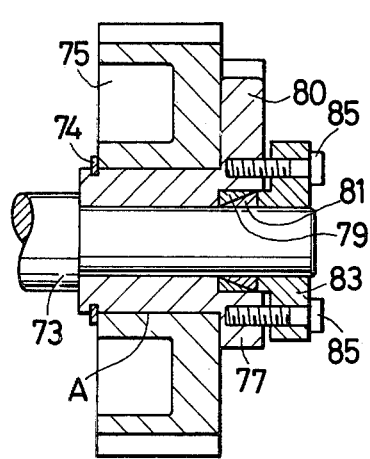
FIGS. 4A and 4B are a sectional view and a plan view showing a fine adjustment mechanism.
Figure 4B:
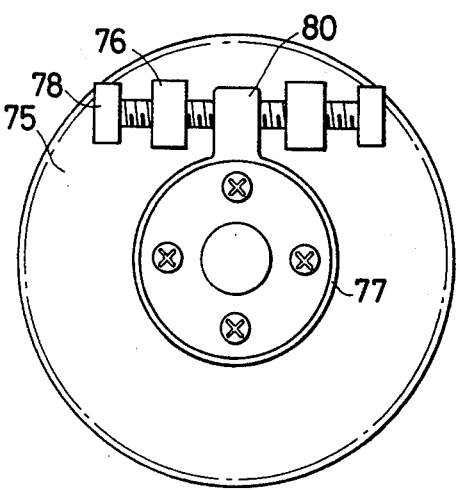

As shown in FIGS. 4A and 4B, the pulley 75 is fixedly secured to the drum shaft 73 by means of the adjusting metal fitting 77. The adjusting metal fitting 77 is tightened to the depressing member 83 adapted to depress the shaft fixing metal fitting comprising the fixing ring 79 and the depressing ring 81. As shown in FIG. 4B, the pulley 75 is provided with metal fittings 76 having female-threads for adjusting screws 78, and the ends of the adjusting screws 78 are in contact with a protrusion 80 of the adjusting metal fitting 77.

The above-described mechanism is assembled as follows. The pulley 75 is placed over the adjusting metal fitting 77 and is then retained by a retaining ring 74 at one end. Then, the adjusting metal fitting 77 is press-fitted over the drum shaft 73. Thereafter, the fixing ring 79 and the depressing ring 81 are placed over the drum shaft 73. Subsequently, the depressing member 83 is placed over the shaft 73 and is temporarily secured to the adjusting metal fitting 77 with the screws 85 in such a manner that the fixing ring 79 and the depressing ring 81 are not tightened yet. In this case, the adjusting screws 78 are set so that they are slightly in contact with the protrusion 80 of the adjusting metal fitting 77. After the belt 89 as shown in FIG. 2A is laid over the pulley 75 to substantially position the first drum 3 and the second drum 5, the screws 85 are tightened to fixedly secure the adjusting metal fitting 77 and the drum shaft 73.

Under this condition, the positional relationship between the first drum 3 and the second drum 5 is not accurate and therefore the fine adjustment is effected by adjusting the adjusting screws 78. In order to turn the drum clockwise as viewed in FIG. 4B, the adjusting screw 78 on the right side is loosened, while the other adjusting screw 78 is tightened. As a result, the adjusting metal fitting 77 is turned clockwise along the contact surface A between the pulley 75 and the metal fitting 77. As the adjusting metal fitting 75 is turned in this manner, the drum shaft 73 is rotated. That is, the drum shaft 73 is turned through the adjusting metal fitting 77 by operating the adjusting screws 78 as described above. Hence, the drums are suitably positioned. After the drums have been positioned, the loosened adjusting screw 78 is tightened, so that the torque of the pulley 75 is applied directly to the adjusting metal fitting 77 or through the adjusting screws 78 to the adjusting metal fitting 77.

In transferring pieces of solid medicine in the external appearance inspecting device shown in FIG. 1A, that is, when the pieces are transferred from the through-holes 32 of the first drum 3 to the holes 52 of the second drum 5, the hole 52 of the second drum 5 should be empty. In other words, if a piece which should be discharged into the acceptable solid medicine transferring pipe 9 or the unacceptable solid medicine transferring pipe 21 is still kept in the hole 52 of the second drum 5, then it may fall off the hole 52 of the second drum 5 to be caught between the first drum 3 and the second drum 5. Furthermore, if the piece of solid medicine is kept in the hole 52 as described above, it may strike the pieces in the through-holes 32 of the first drum 3. Thus, the "jamming" phenomenon may be caused and as a result the driving torque is abnormally increased which will break the pieces. In addition, a part of the drum may be broken by the jamming. Furthermore, the jamming may peel off the black semi-gloss paint which is coated on the inner surfaces of the holes 52 of the second drum 5 to distinguish them from pieces of solid medicine in inspecting their external appearances with the industrial television cameras. Therefore, if such jamming occurs, the conveyance of pieces by the drums must be stopped. Especially, since the inertial force of rotation of the motor is considerably increased, i.e., as the driving force of the motor is transmitted through a reduction gear having a large reduction gear ratio, a force proportional to the square of the reduction gear ratio is applied to the jamming point by the reduction gear. Accordingly, if jamming is caused, it is necessary to disconnect the motor so that the inertial force of rotation of the motor is not applied to the drums, and to brake the motor to quickly stop the motor.

Figure 5A:
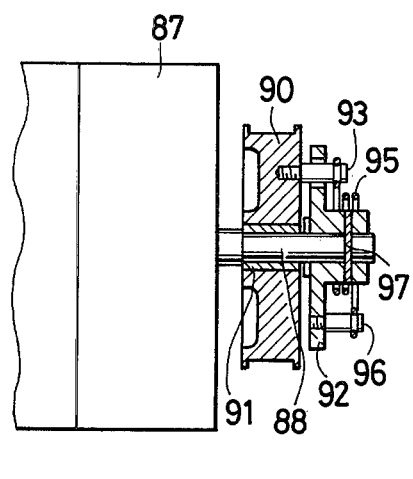
FIGS. 5A and 5B are a sectional view and a front view showing the essential components of a motor drive mechanism.
Figure 5B:
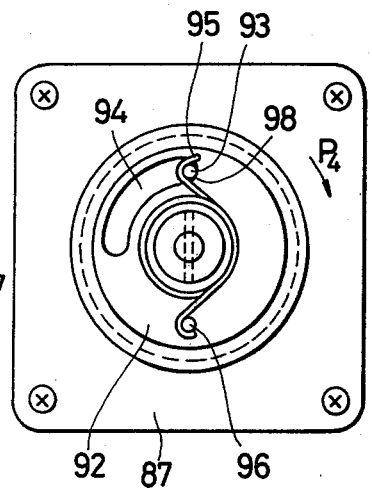

In order to eliminate the above-described difficulties accompanying the occurrence of jamming, the following mechanism is provided according to the invention. This mechanism is as shown in FIGS. 5A and 5B. That is, the mechanism is designed so that when a load other than that required for conveying solid medicine pieces is applied to the first drum and the second drum, the driving force of the motor is not applied to the two drums.

In FIGS. 5A and 5B, reference numeral 87 designates the motor with a reduction gear. A pulley 90 is rotatably mounted on a motor shaft 88 through a bearing 91. The above-described belts are laid over the pulley 90. A driving disk 92 is secured to the motor shaft 88 by a pin 97. An arc-shaped hole 94 is formed in the driving disk 92 as shown in FIG. 5B. A pin 93 secured to the pulley 90 is protruded from the driving disk 92 through the hole 94, whereas a pin 96 is threadingly engaged with or is force-fitted to the driving disk 92. Both end portions of a tortion spring 95 are engaged with the two pins 93 and 96. The pin 93 is in contact with one end 98 of the hole in the case when the motor is rotated in the direction of the arrow P4, and the force of the tortion spring 95 is predetermined to be a value slightly greater than the force which is required to turn the drums.

When the motor 87 is in its normal operation state, i.e., when it is rotated in the direction of the arrow P4 and the pin 93 is maintained depressed against the end 98 of the hole 94 formed in the driving disk 92 by means of the tortion spring 95. Accordingly, the pulley 90 is rotated, and the first drum and the second drum are rotated through the belts laid over the pulley 90. If a load greater than the predetermined value is applied to the drums because of jamming, then a force greater than the set value is applied to the tortion spring 95, as a result of which the pin 93 is disengaged from the end 98 of the hole 94, and only the driving disk 92 is turned. Therefore, tension is applied to the tortion spring 95 and the driving force of the driving disk 92, i.e., the driving force of the motor is absorbed by the tortion spring 95 in this state. Thus, in the case when a load greater than the necessary torque is applied to the drums as in the case of jamming, the application of the driving force of the motor 87 to the drums is immediately restrained.

It is desirable that, at the occurrence of jamming the application of the driving force of the motor 87 to the drums is suspended and simultaneously the motor is braked. For this purpose, in the present invention, the through-holes of the first drum 3 shown in FIG. 2A are detected by an ordinary photo-sensor, and the time intervals of the output pulse signals from the photo-sensor are monitored.

When jamming occurs, the angular speed of the first drum 3 is reduced, and therefore the time intervals of the output pulse signals are increased. In this case, the motor 87 is braked electrically, for instance, by exciting the field coil with DC current, until it is stopped. The through-holes 32 of the first drum 3 are utilized for detecting the variation in angular speed of the first drum 3. This method is advantageous in that even a slight variation in angular speed can be readily detected with high accuracy because several tens of through-holes 32 are positioned at equal intervals on the cylindrical wall of the first drum 3.

When the operation of the external appearance inspecting device is stopped, and especially at the end of a work period, it is necessary to discharge all of the solid medicine pieces to be conveyed by the first drum 3 and the second drum 5. In this case, the following method may be employed: In one of the methods the supply of pieces from the hopper 9 is suspended, and then the pieces of solid medicine left in the chute 11 and in the first drum 3 are discharged by the operator, after the first drum 3 and the second drum 5 have been stopped. Thereafter, the two drums are operated again to discharge the pieces left in the drums 3 and 5 into the unacceptable solid medicine transferring pipe 21.

In a second method, after the supply of pieces from the hopper is stopped, the operations of the drums 3 and 5 are continued until the pieces left in the chute 11 and in the first drum 3 are completely removed, the transferring of the solid medicines from the first drum 3 to the second drum 5 is ended, and the pieces on the second drum 5 are discharged into the acceptable or unacceptable transferring pipes. The solid medicine pieces may be collected by these methods; however, the methods are disadvantageous in that there is a long period of time which elapses from the instant that it is intended to stop the work until the operation is actually stopped.

Accordingly, if the transferring of the pieces of solid medicine from the first drum 3 to the second drum 5 is prevented, then pieces are left in the first drum 3 only, and therefore the time required for collecting the solid medicine can be reduced. The transferring of pieces from the first drum 3 to the second drum 5 may be prevented by stopping the suction of the pieces caused by the negative pressure of the second drum 5. However, this method is still disadvantageous in that the solid medicines sucked and retained by the second drum 5 drop and scatter. In view of the foregoing, a device as shown in FIG. 6 is provided for the external appearance inspecting device according to the invention in order to prevent the solid medicines pieces from being transferred from the first drum 3 to the second drum 5.

Figure 6:
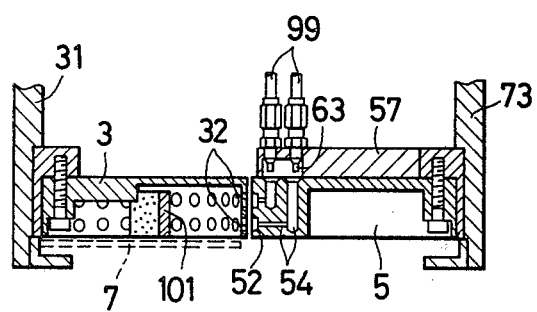
FIG. 6 is a sectional view taken along line D—D in FIG. 2.

FIG. 6 is a sectional view taken along line D—D in FIG. 2A. The through-holes 32 of the first drum 3 coincide completely with the holes 52 of the second drum 5 at the position where the first drum 3 is in contact with the second drum 5 as described before. In this connection, jet nozzles 99 are arranged in the slide plate 57 in contact with the second drum 5 in such a manner that they confront the vacuum suction ports 54 communicating with the holes 52 of the second drum 5 which coincide with the through-holes 32 of the first drum 3. In FIG. 6, reference numerals 31 and 73 designate the drum shaft of the first drum 3 and the drum shaft of the second drum 5, respectively. Reference numeral 7 designates a side plate arranged adjacent to the first drum 3.

The jet nozzles 99 eject no air flow when solid medicine pieces are transferred from the first drum 3 over the second drum. Accordingly, the pieces transferred from the first drum 3 to the second drum 5 are sucked into the empty holes 52 which communicate with the vacuum chamber 63 through the vacuum suction ports 54. When it is required to stop the transferring of solid medicine pieces from the first drum 3 to the second drum 5, the air flows are continuously ejected by the jet nozzles 99 so that the pieces which are otherwise transferred to the second drum 5, are blown into the chamber 34 in the first drum 3. In this manner, solid medicine conveyed being inserted in the through-holes 32 are collected into the chamber 34 in the first drum 3 one after another. If, in this case, a sponge or soft cushion mounted on the side plate 7 protrude in the chamber 34 of the first drum 3, then it will protect the pieces from cracking when they are otherwise struck against the inner walls of the drum by being blown by the jet air flows from the het nozzles 99.

The external appearance inspection device according to the two-drum inside supply system has been described. Now, a three-drum inside supply system in which the above-described supply section of the first drum is replaced by another drum-shaped conveying sectin; that is, functions as a supply section, a first observing section and a second observing section are performed, will be described, with reference to FIGS. 7A and 7B. These figures are a front view and a side view of an external appearance inspecting device according to the three-drum supply system.

A most important difference between the device according to the two-drum inside supply system shown in FIG. 1A and the device according to the three-drum inside supply system shown in FIGS. 7A and 7B resides in that a third drum-shaped conveying section 105 (hereinafter referred to as "a third drum 105" when applicable) is provided as a solid medicine piece supplying section. Solid medicine pieces are supplied from a hopper 111 through a chute 113 into the third drum 3 in a housing 103 so that a predetermined number are stored temporarily therein. The pieces are transferred from the third drum 105 over to a first drum 107, where one surface of each piece is inspected by a first observing 117. Furthermore, the pieces are transferred from the first drum 107 to a second drum 109. As a result each solid medicine piece is turned over to shown the opposite surface thereof which is then inspected by a second observing unit 119.

According to the inspection results provided by the first and second observing units 117 and 119, and the output signal of a sensor 125, or a third observing unit, which inspects the items which cannot be inspected by the first observing unit 117 as the case may be, acceptable and unacceptable pieces of solid medicine are transferred from the second drum 109 into an acceptable solid medicine transferring pipe 121 and an unacceptable solid medicine transferring pipe 123, respectively. The pieces transferred through the pipes 121 and 123 are selectively contained in an acceptable tank and an unacceptable tank (not shown), respectively.

Figure 7A:
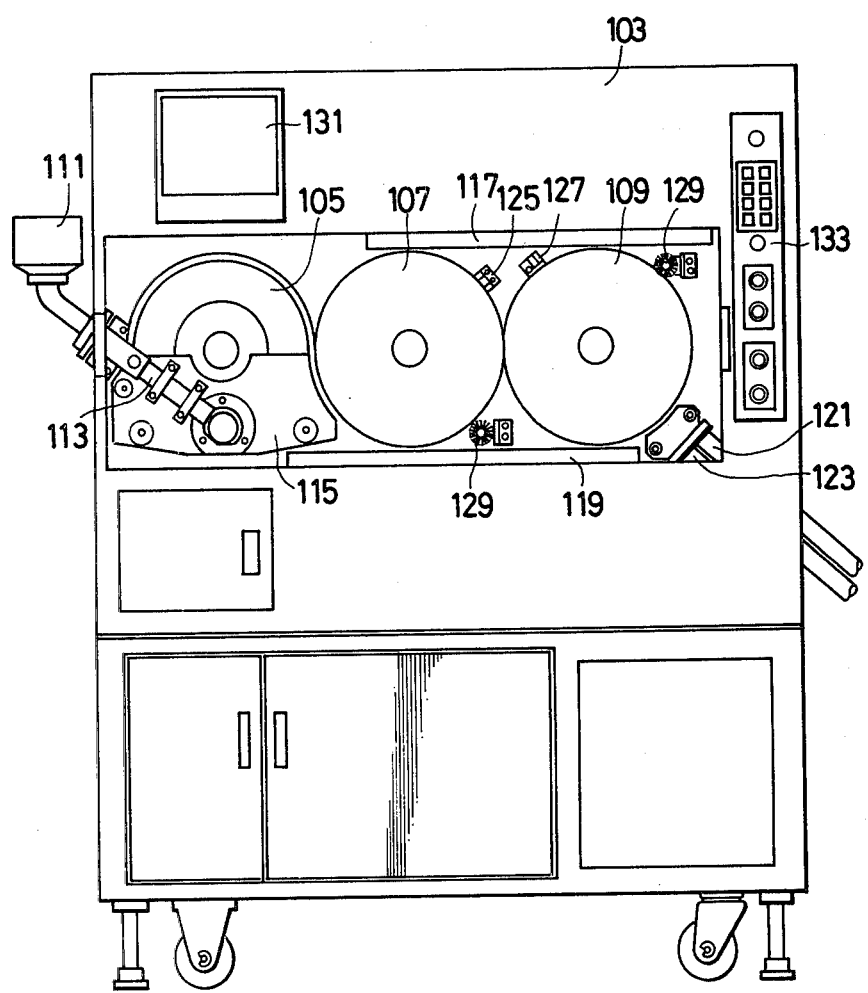
FIGS. 7A and 7B are a front view and a side view showing a second example of the device according to the invention, which is operated in accordance with a three-drum inside supply system.
Figure 7B:
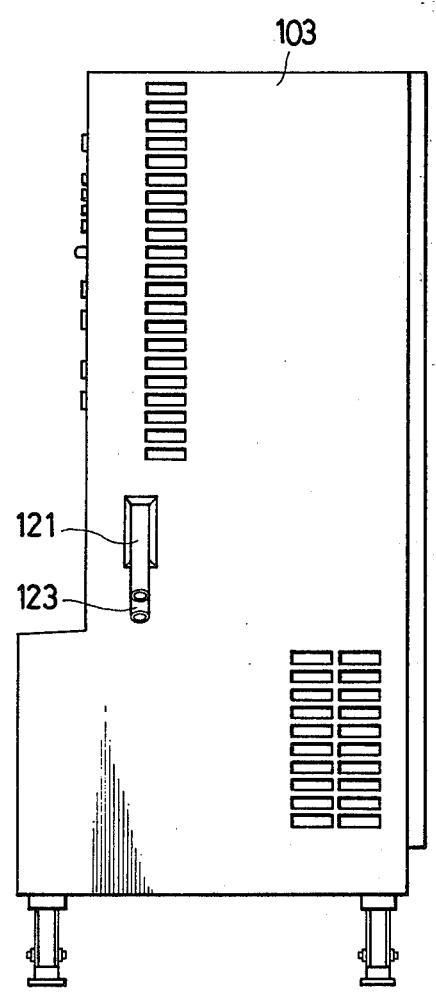

In FIGS. 7A and 7B, the following components are shown. Reference numeral 127 designates a drum position detecting photo-sensor; reference numeral 129, a cleaner brush; reference numeral 131, a monitor television set; and reference numeral 133, a display and operating panel.

Figure 8A:
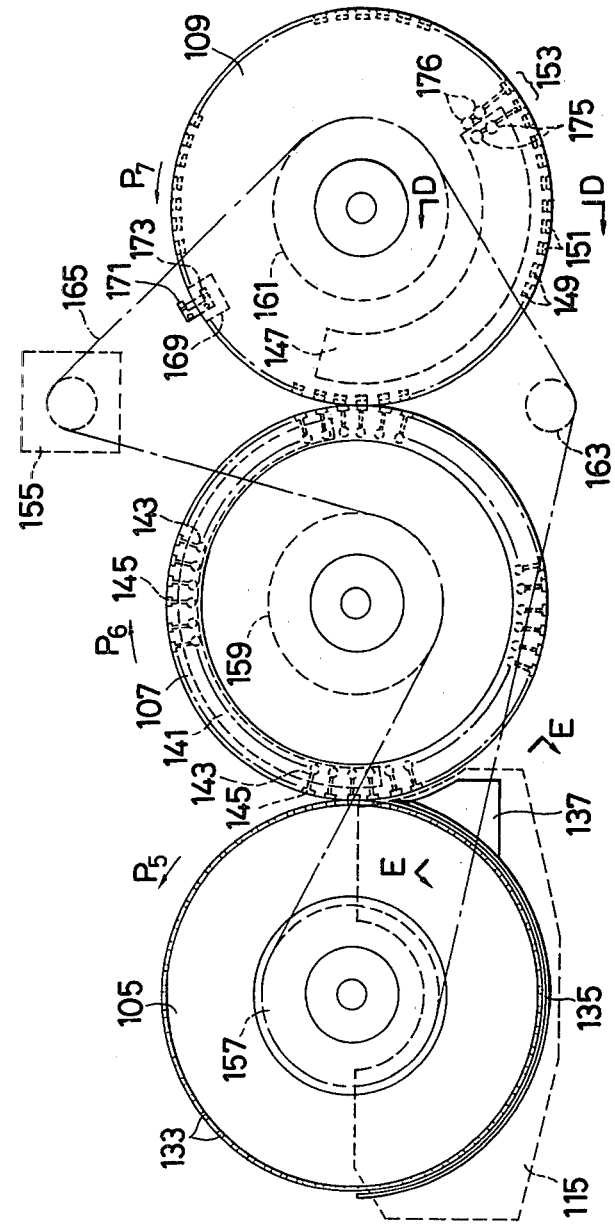
FIG. 8A is an enlarged view of the essential components of drums shown in FIG. 7A.
Figure 9:
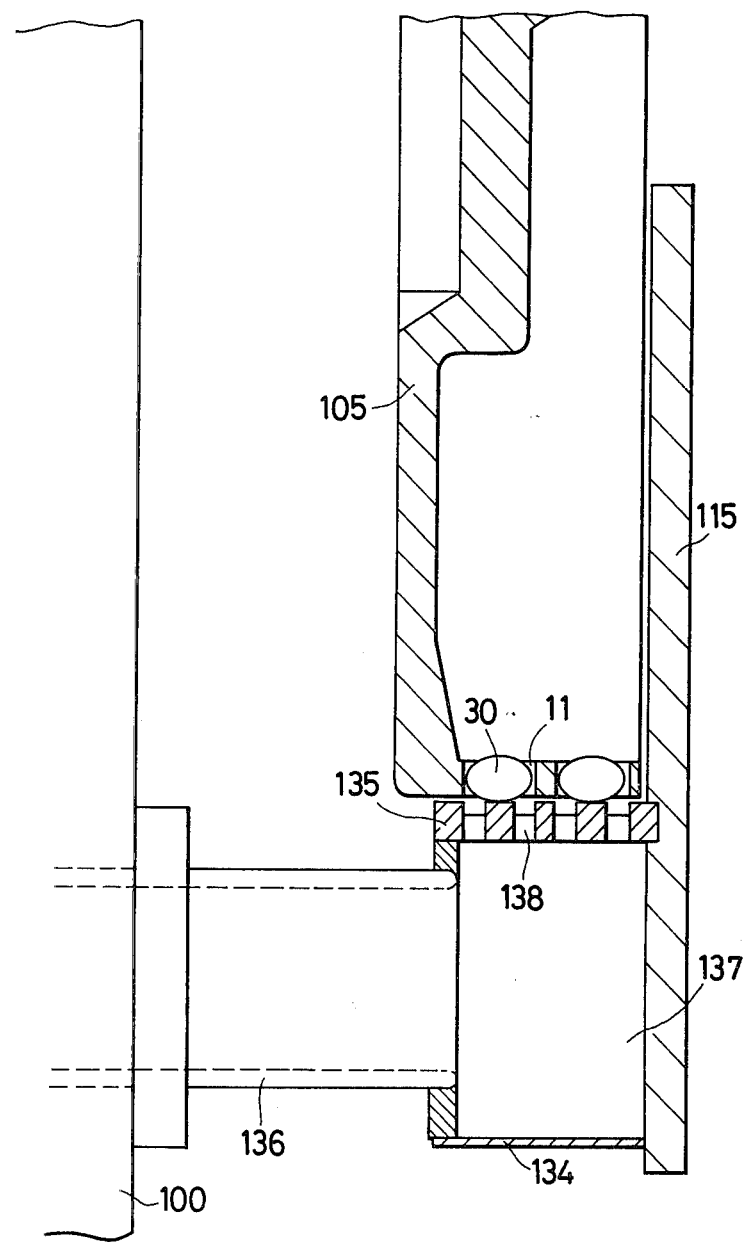
FIG. 9 is a sectional view taken along line E—E in FIG. 8A.

As is apparent from FIG. 8A, the third drum 105 has a plurality of through-holes 133 formed circumferentially in the wall thereof. An outside guide 135 is provided outside the third drum 105 to prevent solid medicine pieces from dropping through the through-holes 133. Furthermore, a negative pressure chamber 137 is provided outside the third drum 105 which, as shown in FIG. 9 a sectional view taken along line E—E in FIG. 8A, is formed by the side plate 115, the outside guide 135, and a negative pressure chamber wall 134. The negative pressure chamber 137 is connected to a suitable negative pressure generating device through a suction pipe extending through a base plate 100, so that a negative pressure is maintained in the chamber 137.

Holes 138 are formed in the outside guide 135 to suck and retain the solid medicine pieces in the third drum 105. The end portion of the outside guide 135 on the side of the negative pressure chamber 137 has V-shaped cuts in such a manner that the centers of the through-holes 133 of the third drum 105 pass through the apexes of the V-shaped cuts. The functions of the negative pressure chamber 137 and the outside guide 135 will be described in conjunction with the operation of the third drum 105 later.

Referring back to FIG. 8A, the first drum 107 has a vacuum chamber 141 and a plurality of holes 145 which communicate with the vacuum chamber 141 through vacuum suction ports 143. The through-holes 133 of the third drum 105 coincide with the holes 145 of the first drum 107 at the position where the third drum 105 is in contact with the first drum 107.

The second drum 109 has a vacuum chamber 147, and a plurality of holes 151 which communicate with the vacuum chamber 147 through vacuum suction ports 149. Similarly, the holes 145 of the first drum 107 coincide with the holes 151 of the second drum 109 at the position where the first drum is in contact with the second drum 109. Discharging jet nozzles 175 and 177 similar to the discharging jet nozzles 69 shown in FIG. 2C are provided for vacuum suction ports 149 communicating with the holes 151 at the portion 153 of the second drum 109 which correspond to the portion where the acceptable and unacceptable solid medicine transferring pipes 121 and 123 are provided. Each vacuum suction port 149 is in the form of an elongated slit.

A driving mechanism comprises an electric motor 155 indicated by the broken line and a belt having teeth on both surfaces thereof and laid over the motor 155 and pulleys 157, 159 and 161 which are respectively secured to the drum shafts of the three drums 105, 107 and 109. The third drum 157, the first drum 107 and the second drum 109 are rotated in the directions of the arrows P5, P6 and P7 by the driving mechanism, respectively. Since the third drum 105 is rotated in the direction of the arrow P5, the solid medicines pieces stored in the third drum 105 are individually inserted into the through-holes 133 and are moved upwardly while being held by the outside guide 135. In this operation, the pieces in the through-holes 133 are sucked by the negative pressure chamber 137, and therefore they are never returned back to the storing section of the third drum 105 from the through-hole 133. The position of each solid medicine piece is held correctly in the through-hole. When the through-holes 133 of the third drum 105 coincide with the holes 145 of the first drum 107, the pieces are transferred from the third drum 105 to the first drum 107.

Figure 10:
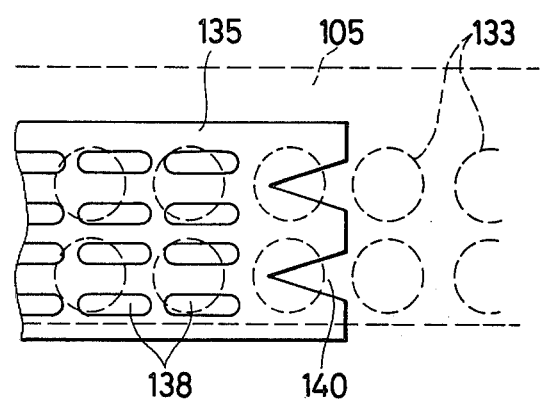
FIG. 10 is a plan view showing an outside guide.

In this operation, the position of each piece is corrected by the outside guide 135. In other words, each solid medicine piece approach the first drum 107 gradually while being supported by two points of the edges of the guide plate 135 which are formed by the V-shaped cuts 140, as shown in FIG. 10. If the cuts 140 are not formed in the outside guide 135, then the solid medicine pieces will abruptly fall as soon as their center of gravity leaves the outside guide. As a result the piece leaps and therefore it may be transferred, in an erect state, into the hole 145 of the first drum. However, as the pieces approach the holes 145 of the first drum 107 gradually because of the cuts 140 of the outside guide 135, the pieces fall into the holes 145 of the first drum 107 slowly; that is, the pieces do not leap.

The solid medicine pieces transferred into the first drum 107 from the third drum 105 are sucked and retained in the holes 145 of the third drum 107 and are moved upwardly. When each piece is brought to the top of the first drum 107, one surface is inspected by the first observing unit 117 shown in FIG. 7A. The piece inspected by the first observing unit 117 is further inspected by the sensor 125. In this case, the items which cannot be inspected by the first observing unit 117, have for instance their thickness inspected. Thereafter, it is transferred into the second drum 109.

Figure 8B:
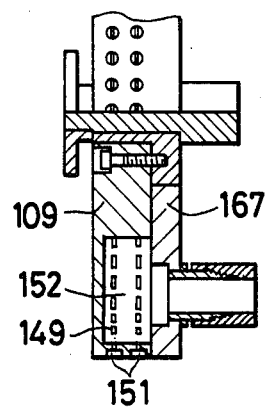
FIG. 8B is a sectional view taken along line D—D in FIG. 8A.

The vacuum chamber 141 of the first drum 107 is formed so that it terminates slightly before the position where the first drum 107 is in contact with the second drum 109 in order to facilitate the transferring of pieces from the first drum 107 to the second drum 107. That is, the vacuum chamber 141 is positioned so that the pieces being transferred are not affected by the effect of the vacuum created in the chamber 141. Since the holes 151 of the second drum 109 communicate with the vacuum chamber 147 through the groove 152 and the vacuum suction ports 149 of the second drum 109 as is shown in FIG. 8B, the solid medicine pieces to be transferred from the first drum 107 to the second drum 109 are sucked and retained in the holes 151 and are moved downwardly.

When each piece is brought to the bottom, or the lowermost end, of the second drum, its opposite surface is inspected by the second observing unit 119 shown in FIG. 7A. After passing through the position of the second observing unit 119, the pieces are sorted out according to the inspection results provided by the first observing unit 117 and the second observing unit 119 and the output signal of the sensor as the case may be. The acceptable solid medicine pieces are transferred into the acceptable transferring pipe 121 while the unacceptable pieces of solid medicine are transferred into the unacceptable transferring pipe 123 by means of the discharging jet nozzles 175 and 177 provided at the portion 153.

Figure 11:
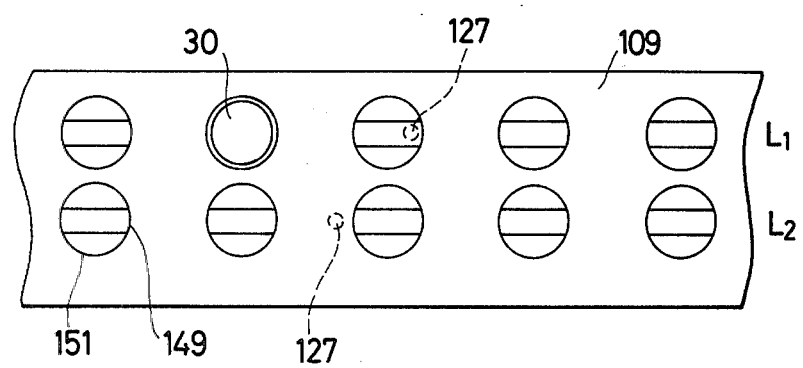
FIG. 11 is a plan view showing the arrangement of a photo-sensor 127 shown in FIG. 8A.

The photo-sensor 127, positioned substantially close to the upper end of the second drum 109 for detecting the position of the drum, comprises a light emitting unit 171 and a photo-transistor 173 which are provided outside and inside of the drum, respectively. The photo-transistor 173 is arranged in the groove 152 of the second drum 109 as indicated by the broken line in FIG. 8B, and the slide plate 167 in contact with the second drum 109 has a cut 169 as indicated by the broken line in FIG. 8A. Each drum position detecting sensor 127 is provided for each of the lines of the holes 151 formed in the outer circumferential wall of the second drum 109 as shown in FIG. 11. The drum position detecting photo-sensors 127 are indicated by the broken lines in FIG. 11.

The positions of the photo-sensors 127 for the two lines $L_1$ and $L_2$ of the holes 151 are obliquely shifted as shown in FIG. 11. The output pulse of the photo-sensor 127 for the line $L_1$ is employed as the position signal of the first drum 107, while the output pulse of the photo-sensor 127 for the line $L_2$ is employed as the position signal of the second drum 109. Since the holes 151 are provided at equal intervals on the cylindrical wall of the drum, the output pulses of each photo-sensor 127 can be utilized as the correct drum position signal. The position signal of the first drum 107 is employed to turn on the illumination device of the first observing unit 117, while the position signal of the second drum 109 is employed to turn on the illumination device of the second observing unit 119.

The illumination devices are electronic flash type light sources. The photo-sensors 127 for the lines $L_1$ and $L_2$ are obliquely shifted as described above. This is to alternately turn on the illumination devices because high voltage must be applied to the electronic flash type light sources. The photo-sensors 127 arranged for the lines $L_1$ and $L_2$ serve not only to detect the positions of the drums but also to detect the solid medicines left in the holes 151. If a piece of solid medicine 30 is placed in the hole 151, the light from the photo-sensor 127 is intercepted by the piece 30. As a result no output pulse is provided by the photo-sensor 127. Accordingly, the time interval of the output pulses of the photo-sensor 127 is increased if a piece of solid medicine is left in the hole. That is, the presence of the solid medicine left in the hole can be detected by monitoring the time interval of the output pulses. In the case where a piece left in the hole is detected, in this manner, occurrent of jamming can be prevented by quickly stopping the motor.

The drum position may be detected by using holes formed at equal intervals in the cylindrical wall of the drum and a photo-sensor. This is similar to an ordinary method for detecting the position of a rotary body in which holes are formed at equal intervals in the cylindrical wall of the rotary body and the holes are detected by a photo-sensor. However, by the utilization of the holes 151 of the second drum 109, the positions of the drums can be detected with high accuracy because the holes 151 are provided at equal intervals on the cylindrical wall of the drum. Furthermore, the utilization of the holes 151 of the second drum 109 is advantageous in that pieces of solid medicine left in the holes can be detected.

Figure 8C:
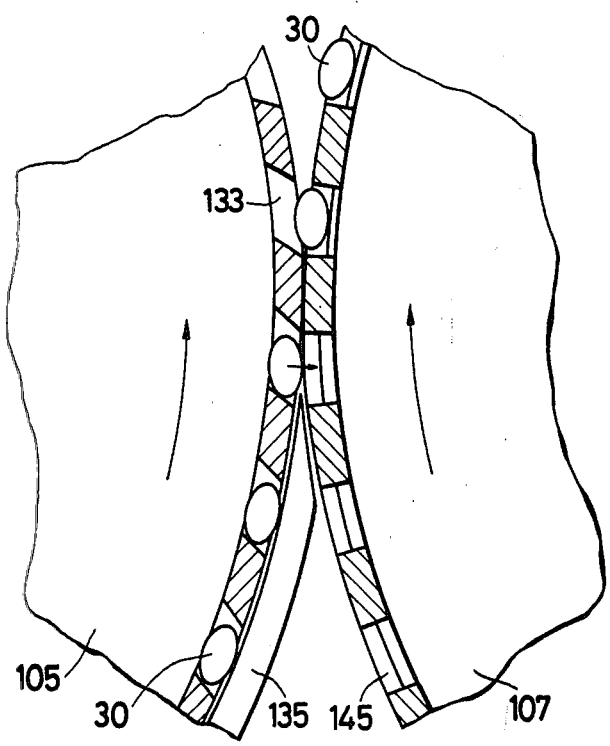
FIG. 8C is a sectional view showing the essential components of another example of a third drum shown in FIG. 8A.

The through-holes 133 of the third drum 105 are cut perpendicularly to the direction of rotation of the drum. However, the through-holes 133 may be cut so that, as shown in FIG. 8C, the axis of each through-hole 133 forms an angle of 30° with the direction of rotation of the drum. In the latter case, a piece of solid medicine 30 in a through-hole 133 is supported by the wall forming the through-hole 133 until it is brought to the position where it is transferred to the first drum 107. It will not drop into the storing section of the third drum 105. Each piece is held by the wall of the through-hole 133 and the outside guide 135 as is apparent from FIG. 8C. Therefore, the piece of solid medicine is transferred in a correct posture from the third drum 105 to the first drum 107.

When, the piece is not supported by the wall of the through-holes 133, its center of gravity is shifted from the outside guide 135. Then sometimes it inclines and falls down in the hole 145. However, since the axis of the through-hole 133 forms an angle with the direction of the rotation of the drum as described above, the piece of solid medicine is supported by the wall of the through-hole 133 and by the outside guide 135 and the piece is retained by the wall of the through-hole 133 until it leaves the outside guide 135. Therefore, a phenomenon where the piece is sucked, in an inclined state, into the hole 145 of the first drum 145, will not result. That is, the piece is sucked and retained in a correct posture in the hole 145 of the first drum 107.

The above-described examples of the external appearance inspecting device according to the invention employ the two-drum inside supply system and the three-drum inside supply system, respectively, in which the pieces of solid medicine are supplied from inside the drum. Now, another example of the external appearance inspecting device according to the invention will be described with reference to FIGS. 12A and 12B. The external appearance inspecting device shown in FIGS. 12A and 12B is operated in accordance with a three-drum outside supply system in which three drums are employed and pieces of solid medicine are supplied from outside the drum.

Figure 12B:
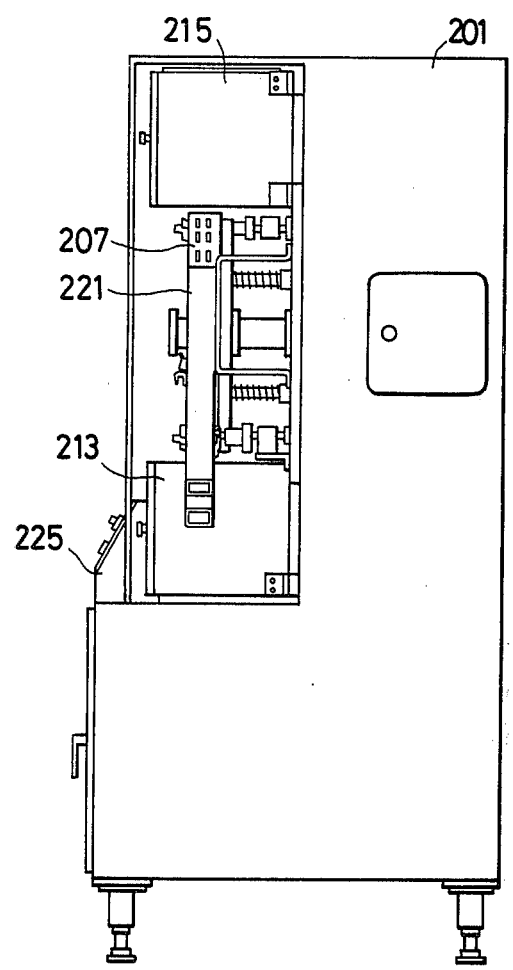
Figure 13A:
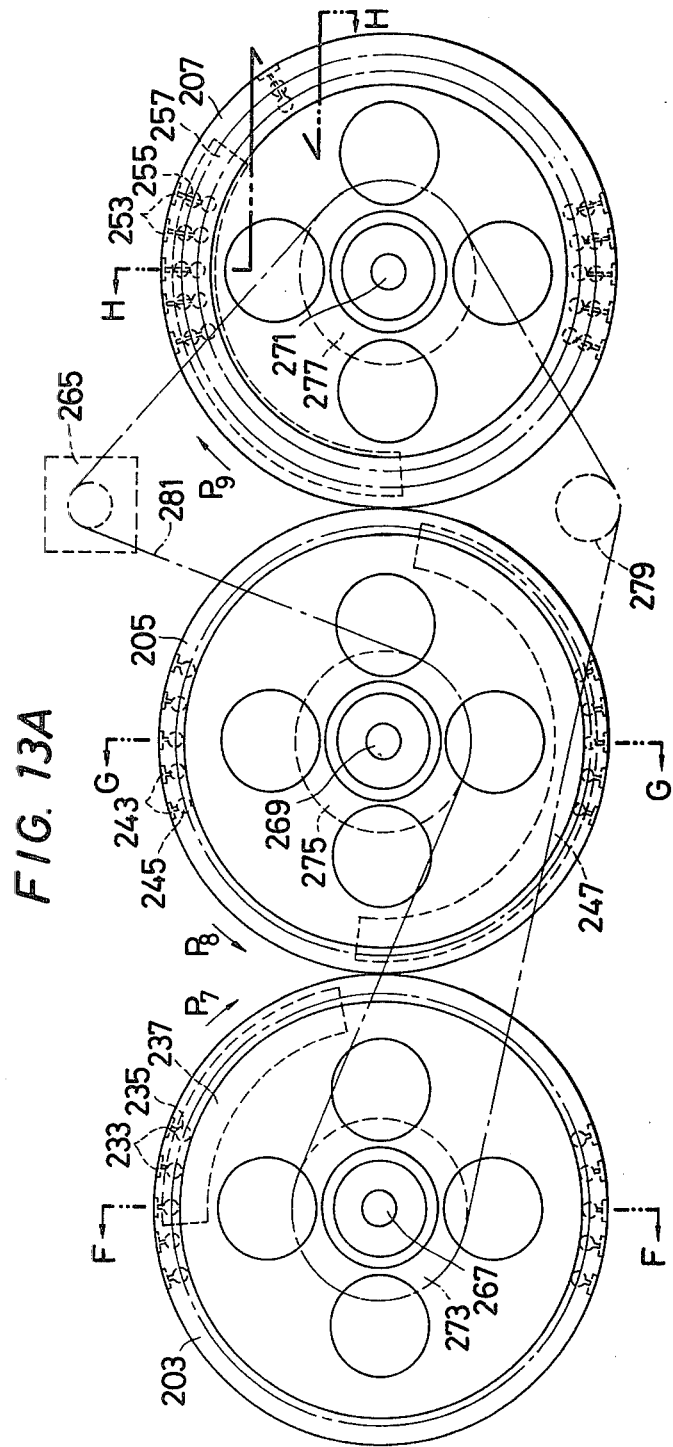
FIG. 13A is an enlarged view showing the essential parts of drums in FIG. 12A.

Referring to FIGS. 12A and 12B, a third drum 203, a first drum 205 and a second drum 207 are arranged in a housing 201. A container 211 is provided in the vicinity of the third drum 203. A predetermined amount of solid medicine are supplied from a hopper 209 into the container 211 and stored therein. A first observing unit is provided in a box 213 provided close to the first drum 205, and a second observing unit is provided in a box 215 provided close to the second drum 207. An acceptable transferring pipe 217 and an unacceptable transferring pipe 219 are provided in the vicinity of the second drum 207. The acceptable transferring pipe 217 is coupled to a chute 221 to an acceptable storing tank 223. In FIG. 12A, reference numeral 225 designates an operating panel: reference numeral 227, a control box; reference numeral 229, a monitor television set; and reference numeral 231, a cleaning brush.

As shown in FIGS. 13A, 13B, 13C and 13D, the third drum 203 has a plurality of holes 233 provided at equal intervals on the circumferential wall thereof. The holes 233 communicate through the respective vacuum suction ports 235 with a vacuum chamber 237 provided in the slide plate 239, which is evacuated through a suction pipe 241. The vacuum chamber 237 terminates at a position above the position where the third drum 203 is in contact with the first drum 205. The first drum 205 has a plurality of holes 243 formed at equal intervals in the circumferential wall thereof. These holes 243 communicate with a vacuum chamber 247 through vacuum suction ports 245, respectively. The vacuum chamber 247 is provided in a slide plate 249 and is evacuated through a suction pipe 251. The end portion of the vacuum chamber 247 close to the third drum 203 is above the position where the third drum 203 is in contact with the first drum 205, while the opposite end portion of the vacuum chamber 247 close to the second drum terminate below the position where the first drum 205 is in contact with the second drum 207.

The second drum 207 has a plurality of holes 253 formed at equal intervals in the circumferential wall thereof. The holes 253 communicate with a vacuum chamber 257 through vacuum suction ports 255. The vacuum chamber 257 is provided in a slide plate 259 and is evacuated through a suction pipe 261. The end portion of the vacuum chamber 257 close to the first drum 205 extends below the position where the first drum 205 is in contact with the second drum 207. The second drum 207 is provided with two discharging jet nozzles 263 which are fixedly secured to the slide plate 259. The discharging jet nozzles 263 are so provided that the jet flows from the nozzles are applied to the holes 253 through the vacuum suction ports 255, respectively.

The first, second and third drums are rotated by a driving mechanism made up of an electric motor 265 and a belt 281 with teeth on both sides thereof. The belt 281 is laid over the motor 165, pulleys 273, 275 and 277 fixedly secured respectively to the drum shafts 267, 269 and 271 of the drums, and a tension pulley 279. The third drum 205, the first drum 207 and the second drum 209 are rotated in the directions of the arrows P6, P7 and P8, respectively.

Figure 14A:
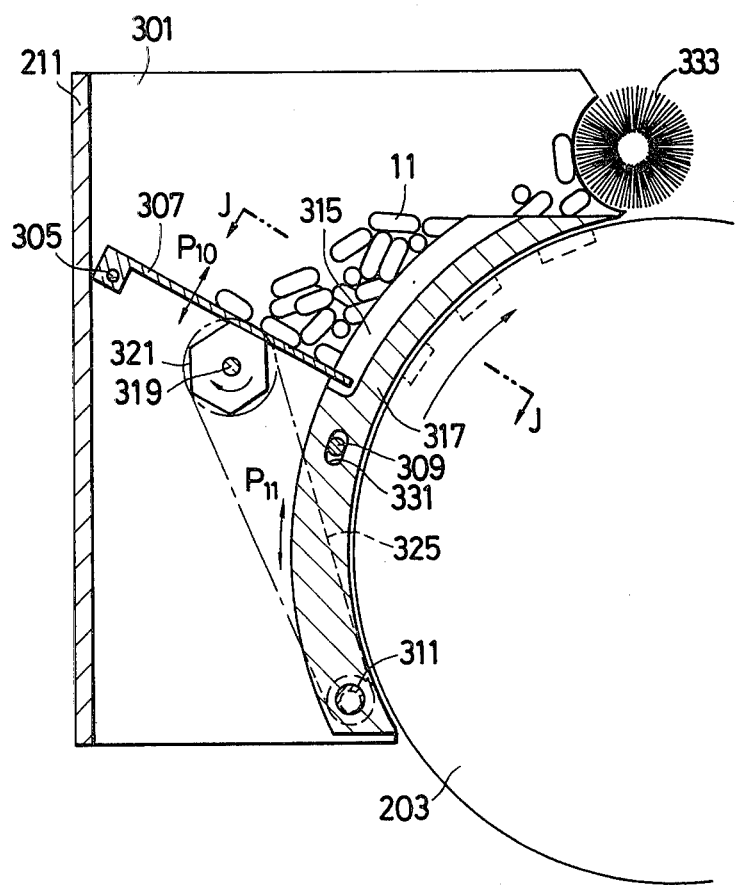

The container 211, shown in FIG. 12A, for supplying pieces of solid medicine to the third drum 203 is constructed as shown in FIGS. 14A and 14B. The container 211 has two side plates 301 and 302. Provided between the side plates 301 and 302 are a swinging plate 307 which is swingable about a shaft 305, and partition boards 313, 315 and 317 which are supported by a shaft 309 and an eccentric cam 311. The partition boards 313, 315 and 317 are curved along the circumferential wall of the third drum 203. The central partition board 315 extends higher than the other partition board 313 and 317 as shown in FIG. 14C. The end portion of the swinging plate 307 is interdigitated with the partition boards 313, 315 and 317. The swinging plate 307 is swung back and forth in the directions of the arrow P10 by a hexagonal prism 321, or a driving cam, which is fixedly secured to a shaft 319 coupled to an electric motor.

A pulley 327 is fixedly mounted on a shaft 329 coupled to the aforementioned eccentric cam 311. A belt 325 is laid over the pulley 329 and a pulley 323 which is fixedly secured to the shaft 319 of the driving cam 321. Therefore, the pulley 327 is driven through the belt 325 by the pulley 323, and the pulley 327 transmits its torque to the eccentric cam 311 through the shaft 329. When the eccentric cam 311 is rotated, the partition boards 313, 315 and 317 are reciprocated in the directions of the arrow P11 because a stationary shaft 309 passes through an elongated hole 331. A brush 333 for arranging pieces of solid medicine are provided at the upper end of the third drum 203.

Immediately after the drums are operated, the swinging plate 307 and the partition boards 313, 315 and 317 are operated to vibrate the pieces 11, shown as capsules 11 in FIG. 14A, supplied to the container 211. The pieces thus vibrated are placed between the partition boards 313, 315 and 317, and are then inserted in the holes 233 of the third drum 203. Since the vacuum chamber 237 of the third drum 203 does not extend to a position corresponding to the position of the container 211, the pieces sucked and retained in the holes 233 of the third drum 203 are in correct posture at all times. That is, the pieces are vibrated by the swinging plate and the partition boards 313, 315 and 317 until they are placed in correct posture in the holes 233. The remaining pieces which have not been placed in the holes 233 of the third drum 203 are conveyed upwardly on the circumferential wall of the third drum 203 and are then returned into the container 211 by means of the brush 333. The pieces placed in the holes 233 of the third drum 203 in the container 211 are sucked and retained in the holes 233 because the holes 233 are evacuated by the vacuum chamber 237 when the holes 233 reach the upper end portion of the drum. The pieces in the holes 233 are maintained by the evacuation effect of the vacuum chamber and will not fall off until they are transferred from the third drum 203 over to the first drum 205.

The pieces are transferred from the third drum 203 to the first drum 205 at the position where the third drum 203 is in contact with the first drum 205. When each piece of solid medicine sucked and retained in the hole of the first drum 205 is brought to the lower end portion of the drum, its one surface is inspected by the first observing unit provided in the box 213 shown in FIG. 12A. After being inspected by the first observing unit, the piece is further inspected by the sensor 214 for items which cannot be inspected by the first observing unit.

The piece of solid medicine passing through the position of the sensor 214 is transferred from the first drum 205 over to the second drum 207 at the position where the first drum 205 is in contact with the second drum 207. When the piece transferred into the second drum 207 is conveyed to the upper end portion of the drum, its opposite surface, which was not inspected by the first observing unit, is inspected by the second observing unit provided in the box 215 shown in FIG. 12A. When the piece is conveyed to the position of the discharging jet nozzles 263 after being inspected by the second observing unit, it is classified into acceptable and unacceptable designations according to the inspection results provided by the first and second observing units and by the output signal of the sensor 214.

The acceptable solid medicine pieces are delivered into the acceptable transferring pipe 217 while the unacceptable pieces are delivered into the unacceptable transferring pipe 219. The holes 253 of the second drum 207 communicate with the independent discharging jet nozzles 263, and therefore the pieces in the holes 253 can be positively discharged separately according to these classifications.

In the above-described examples, the first drum and the second drums are provided with the holes to receive the pieces of solid medicine. In this connection, it is preferable to construct the first drum as shown in FIG. 15 in order to reduce the distance required for transferring pieces thereby to positively transfer the pieces with less mechanical impact.

Figure 15:
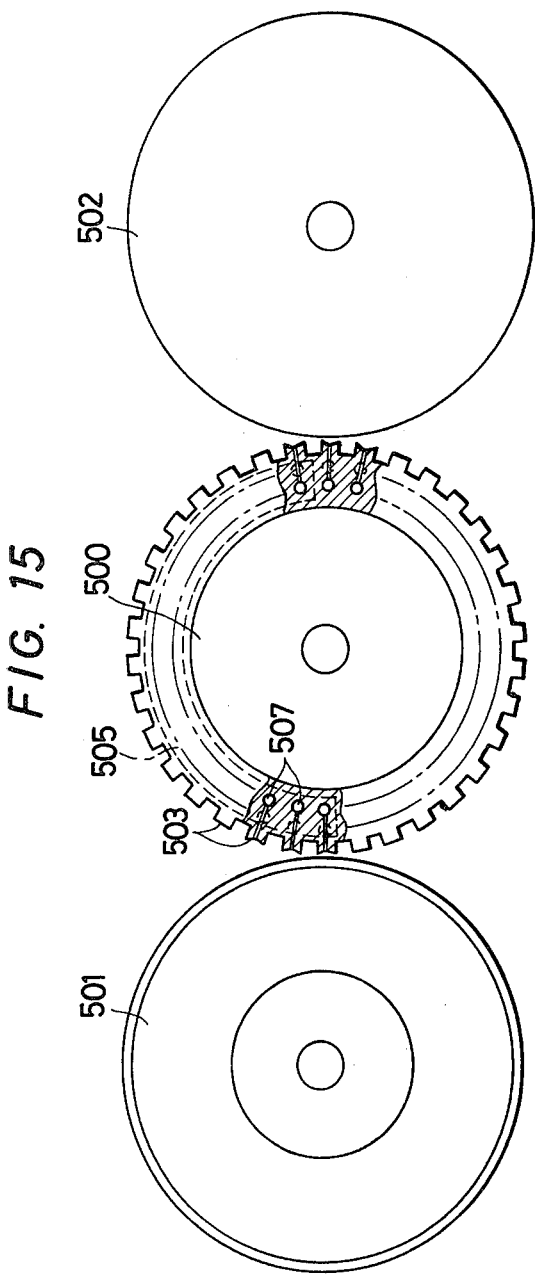
FIG. 15 is an enlarged view showing another example of a hole adapted to reveive a piece of solid medicine.

In FIG. 15, the first drum 500 between the third drum 501 and the second drum 502 has accommodating protrusions 503 instead of the holes, for receiving the pieces. The solid medicine accommodating surfaces of the accommodating protrusions 503 are like recesses. The accommodating protrusions 503 have vacuum suction ports 507 at the bottoms of the recesses thereof, which communicate with a vacuum chamber 505, to positively place the pieces in the recesses of the accommodating protrusions 503 with the aid of the negative pressure in the vacuum chamber 505. The solid medicine transferring distance is reduced by the provision of the accommodating protrusions 503. As a result, the possibility of leaping or damaging the pieces is considerably reduced, the thickness and acceptability of each piece can be readily determined, and the side can be observed. These are merits derived from the provision of the accommodating protrusions 503.

Also, if the second drum 502 is constructed similar as in the first drum 500, the solid medicine transferring distance is further reduced, and the same effects as described above can be obtained.

Figure 16:
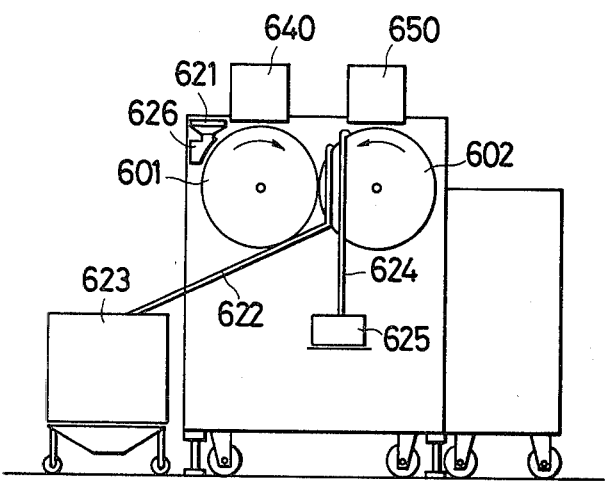
FIG. 16 is a front view showing a fourth example of the device according to the invention.

Shown in FIG. 16 is a fourth example of the external appearance inspecting device according to the invention, which is compact in arrangement, and is operated in accordance with the two-drum outside supply system. In this two-drum outside supply system, two drums are employed and pieces of solid medicine are supplied from outside the drum. A first drum 601 itself has a solid medicine supplying function, and a hopper 621 and a container 626 serves as the solid medicine supplying section as shown in FIG. 14A.

Referring to FIG. 16, the first drum 601 and a second drum 602 are arranged in a housing. The container 626 is provided in the vicinity of the first drum 601. A predetermined amount of solid medicine are supplied from the hopper 621 into the container 626 and stored therein. A first observing unit 640 and a second observing unit 650 are provided above the first drum 601 and the second drum 602, respectively. The surfaces of the solid medicine are inspected by the first and second observing units 640 and 650. Similarly as in the case of FIGS. 1A and 1B or FIGS. 12A and 12B, it is classified into an acceptable or unacceptable group according to the general determination of the output signals of the first and second observing units.

This example is advantageous for the folowing points: The maintenance and inspection of the observing units can be readily achieved because both of them are provided above the drums. The entire device according to the two-drum system can be made very compact. However, in view of the maintenance and inspection of the rotary mechanism, it is advisable that the device is made in accordance with the three-drum system in which the third drum serves as the solid medicine supplying section, because each function is performed by separate drums.

The above-described transferring mechanism is one of the specific features of this invention. In addition, another specific feature of the invention, which is a general determination system with recognition devices, will be described with reference to FIG. 17.

Figure 17:
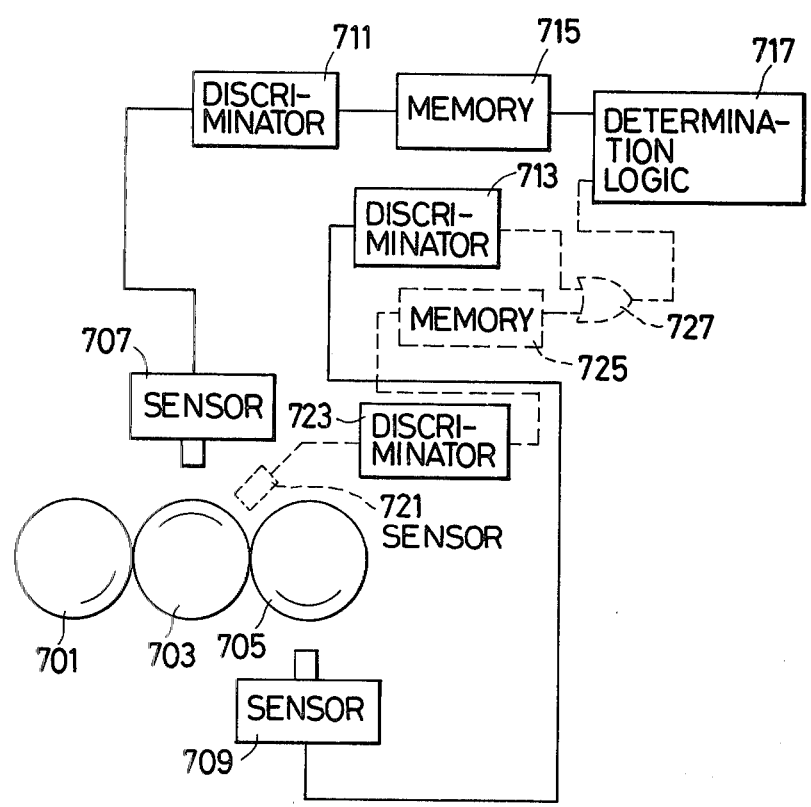
FIG. 17 is a block diagram showing an external appearance inspecting circuit.

FIG. 17 is a diagram for a description of the general determination system in the case of three drums; however, the same determination system can be applied to the case of two drums. In FIG. 17, reference numerals 701, 703 and 705 designate a third drum, a first drum, and a second drum, respectively; reference numeral 707, a first observing unit; and reference numeral 709, a second observing unit.

Each piece of solid medicine is transferred from the third drum 701 to the first drum 703, and it is then conveyed by the first drum 703 to the first observing unit 707, where its one surface is inspected. The first observing unit 707 is an industrial television camera. In general, in the case where the external appearance inspection or pattern recognition of an object is conducted with an industrial television camera, an electronic flash means or a mechanical or electrical shutter is employed to provide a stationary image of the object. Hence, when the object arrives at a predetermined position the television camera takes the image thereof. In this example also, such means (not shown) are employed. A sensor having not only the above-described function but also a function of detecting delicate hue which cannot be detected by the television camera, may be employed.

The output signals of the television camera and the sensor are applied to a first discriminating device 711, where the scratch, roughness and size of the surface of a solid medicine are discriminated according to well known pattern recognition techniques. The discrimination signal of the first discriminating device 711 is stored in a memory device 715 comprising, for instance, shift registers, in the form of one bit signal when it is simple, or in the form of plural bits signal when it includes a plurality of factors. This signal thus stored is shifted one stage whenever a piece of solid medicine is discriminated. In the case where the memory device is an ordinary random access memory, the contents of the memory device are shifted to the next address whenever a piece is discriminated.

When the solid medicine is transferred from the first drum 703 to the second drum 705, it is turned over to expose the opposite surface, which is inspected by a second observing unit 709. Then, the solid medicine is subjected to discrimination by a second discriminating device 713 as to whether it is acceptable or not according to the output of the second observing unit 709. If a memory device 715 is a shift register, then the capacity of the shift register is set to be equal to the number of pieces of solid medicine existing between the position immediately below the first observing unit 707 and the position immediately below the second observing unit 709 (more precisely, the number of solid medicine accommodating holes). In this case, immediately upon reciept of the discrimination signal of the opposite surface of a solid medicine by the second discriminating device, the discrimination signal of the one surface of that piece of solid medicine is read out of the last stage of the memory device 715. Thus, a general determination logic device 717 can determine whether the solid medicine is acceptable or not according to the two discrimination signals.

The general determination system according to the invention is more effective in the case where one surface of a piece of solid medicine is different in external appearance from the opposite surface thereof, because it is not practical to determine whether the entire surface of a piece is acceptable or not merely by observing only one surface thereof. For instance, in the case where a piece in which one surface is white and the opposite surface is yellow is acceptable, the general determination is absolutely required to determine piece whose both surfaces are white or yellow unacceptable. This is because it is apparent from the mode of supplying solid medicine that the surface of a piece first confronting with the first observing unit is not always constant. That is, the white surface may first confront with the first observing unit, or the yellow surface in the case of a subsequent piece.

The general determination system according to the invention is effective in the case also where both surfaces are identical in external appearance, due to the following reasons. In the case where the mechanism (corresponding to 19 and 21 in FIG. 1A) for distributing the solid medicines separately according to the classifications is provided at one position, namely, at the position of the second drum, it is necessary to input the discrimination signal according to the output of the first observing unit into the memory device and to shift it therein. This is done because the output of this memory device and the discrimination signal according to the output of the second observing unit should be utilized simultaneously. Accordingly, statistical treatment such as investigation of the frequency of creation of pieces of solid medicine whose both surfaces are unacceptable can be performed by the utilization of the general determination system. The above-described discriminating devices may be replaced by a single discriminating device which is operated in time division manner.

In the above-described general determination system, the acceptability of a piece is determined according to the inspection results provided by the first observing unit 707 and the second observing unit 709. The case in which the general determination is performed by inspecting an item which cannot be inspected by the first observing unit 707 and the second observing unit 709, for instance the thickness of a solid medicine will now be described. This inspection can be achieved by adding a circuit indicated by the broken line in FIG. 17.

Figure 18:
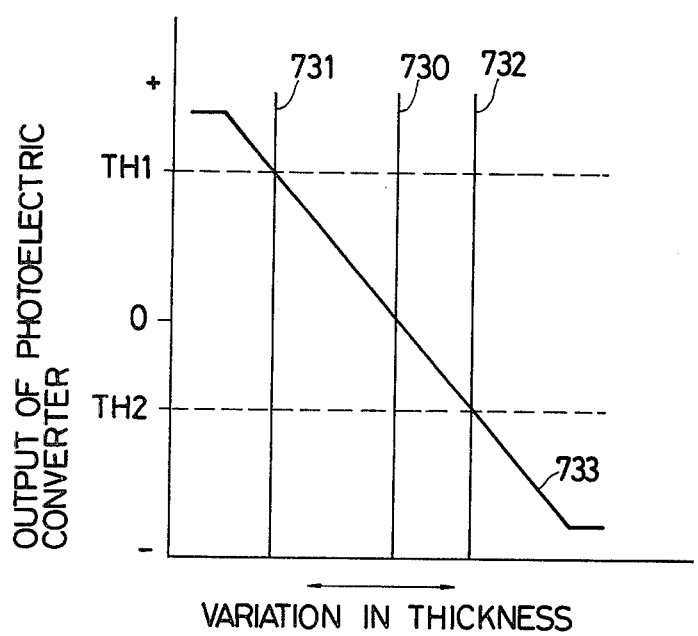
FIG. 18 is a graphical representation showing the output characteristic curve of a photoelectric converter in a sensor 21 shown in FIG. 1.

The sensor 721 comprises the light emitting unit 20 and the photoelectric converter 24 shown in FIG. 3A. The output of the sensor 721 is set as indicated in FIG. 18, in which the horizontal axis represents variations in thickness of a piece of solid medicine and the vertical axis represents outputs of the photoelectric converter. It is assumed that the output curve 733 of the photoelectric converter is such that the photoelectric converter provides a reference output 0 with respect to the line 730 indicating a reference thickness. Then, in the case where a thinner piece is inspected by the sensor, the amount of light interception is reduced as much and accordingly the quantity of light applied to the photoelectric converter is increased. As a result the output is increased.

In the case where a thicker piece is inspected, the amount of light interception is increased as much and accordingly the quantity of light applied to the photoelectric converter is decreased. The output then is decreased. If the minimum allowable thickness is indicated by the line 731, then the output threshold value is at $TH_1$. If the maximum allowable thickness is indicated by the line 732, then the output threshold value is at $TH_2$. Thus, if the output is within the range of from $TH_1$ to $TH_2$, then the thickness of the solid medicine is determined as being acceptable.

In FIG. 17, the output of a third observing unit, namely, the sensor 721 is applied to a third discriminating device 723, where the acceptability of the piece is determined.

The discrimination signal of the third discriminating device 723 is stored, as a one-bit signal, in a memory device 725 comprising a shift register. The signal stored in the memory device 725 is shifted whenever a piece is discriminated by the discriminating device 723. The capacity of the shift register forming the memory device is set to be equal to the number of pieces existing between the sensor 721 and the second observing unit 709.

The logical sum of the output of the memory device 725 and the output of the second discriminating device 713 adapted to decide the output of the second observing unit is obtained by an OR circuit 727. The output is applied to the general determination device 717. The use of the OR circuit 727 is due to the following reason. The output signal lines of the memory device 725 and the discriminating circuit 713 are representative of unacceptable solid medicines. If these output signal lines are representative of acceptable pieces, then an AND circuit should be employed instead of the OR circuit.

As is apparent from the above description, according to the invention, the aforementioned condition (b) of the objects can be satisfied by automatically turning over a piece of solid medicine by the use of at least two drum-shaped conveying sections, and condition (a) can be met by utilizing one of the two drum-shaped conveying sections or a third additional drum-shaped conveying section as the solid medicine supplying section. Furthermore, condition (c) can be satisfied by providing the memory devices. Since a mechanism such as belt conveyers which may be laid over a long distance is not employed in the device, the device is simply constructed and the maintenance and inspection thereof can be readily achieved. Thus, the condition (d) is satisfied.

In the above description, the observing unit is the industrial television camera; however, the invention is not limited thereto or thereby. That is, it may be a two-dimensional image pick-up means such as a solid matter image pickup camera. It is apparent that other modifications and improvements can be made without departing from the essential concepts herein.

What is claimed is:

1. A device for inspecting the external appearance of pieces of solid medicine, comprising: a solid medicine piece supply section; a first drum-shaped conveying section for conveying pieces of solid medicine supplied by said supplying section at equal intervals so that one surface of each piece of solid medicine is observed; a second drum-shaped conveying section for receiving the pieces from said first drum-shaped conveying section and conveying the pieces at equal intervals so that an opposite surface of each piece is observed; first and second sensor means provided adjacent to said first drum-shaped conveying sections for observing both surfaces of each piece of solid medicine respectively; means for rotating said first and second drums; first and second discriminating means for determining whether each piece of solid medicine is acceptable or unacceptable according to observation results provided by said first and second sensors; adjustment means for positioning said first and second drums relative to each other, said adjustment means comprising an adjusting metal fitting fitted around one end of a drum shaft of one of said first and second drums, a pulley secured to said drum shaft through said adjusting fitting, a depressing member adapted to depress said adjusting fitting for fixing said fitting to said drum shaft, screws for loosening and tightening said depressing member to facilitate coarsely adjusting a relative phase of said one of said first and second drums relative to said drum shaft, a protrusion extending rigidly from said adjusting metal fitting, first and second metal fittings extending rigidly from said pulley on opposed sides of said protrusion and having threaded holes provided therein, and first and second adjusting screws fitted through said threaded holes of said first and second metal fittings, respectively, and having ends abutting said protrusion; said adjusting screws providing a fine adjustment of said relative phase; and memory means for storing solid medicine piece discrimination signals produced on the basis of the observation results provided by said first sensor, the discrimination signal based on the observation result provided by said second sensor and the discrimination signals stored in said memory means being supplied to a general determination logic means to determine whether the external appearance of each piece of solid medicine is acceptable or unacceptable.

2. A device as in claim 1, wherein said supplying section is formed as a third drum-shaped conveying section and means for rotating said third drum.

3. A device as in claim 2, wherein said third drum-shaped conveying section has a through-hole communicating the outside of said third drum-shaped conveying section with the inside of the same to store pieces of solid medicine therein.

4. A device as in claim 2, wherein said third drum-shaped conveying section has solid medicine piece receiving holes formed in the outer circumferential wall thereof, whereby pieces of solid medicine are supplied into said holes from outside said drum.

5. A device as in claims 1 through 4, wherein each of said first and second drum-shaped conveying sections has accommodating protrusions with solid medicine piece accommodating recesses, said recesses provided at equal intervals on the outer circumferential wall thereof.

6. A device as in claim 5, wherein each accommodating protrusion communicates through a vacuum suction port with a vacuum chamber provided in said drum.

7. A device as in claim 1, wherein said first drum-shaped conveying section has a through-hole communicating the outside of said first drum-shaped conveying section with the inside of the same to store pieces of solid medicine therein.

8. A device as in claim 1, wherein said first drum-shaped conveying section has solid medicine piece receiving holes formed in the outer circumferential wall thereof and whereby solid medicine pieces are supplied into said holes from outside said drum.

9. A device as in claims 7 or 8, wherein said second drum-shaped conveying section has accommodating protrusions with solid medicine piece accommodating recesses, said recesses provided at equal intervals on the outer circumferential wall thereof.

10. A device as in claim 9, wherein each accommodating protrusion communicates through a vacuum suction port with a vacuum chamber provided in said drum.

11. A device as in claims 1, 2, 3, 4, 7 or 8 further comprising a third sensor for observing the thickness of each piece of solid medicine.

12. A device as in claim 11, wherein said third sensor is positioned prior to the point of observation by said second sensor.

13. A device as in claim 11 further comprising third discriminating means receiving the output of said third sensor and determining the acceptability of each piece based on an acceptable range of thickness.

14. A device as in claim 13, wherein said third sensor comprises a source of light and a photoelectric convertor positioned on opposite sides of said piece of solid medicine, said photoelectric convertor producing an output signal dependent on the amount of light interception created by said piece of solid medicine.

15. A device as in claim 13 further comprising second memory means for storing the output of said third discriminating means.

16. The device as in claim 15 further comprising logic means responsive to the outputs of said second memory means and said second discriminating means and providing an output signal to said general determination logic means.

17. The device as in claim 16, wherein said outputs are representative of unacceptable pieces and said logic means comprises an OR gate.

18. The device as in claims 1 or 11 further comprising separating means for selectively separating pieces of solid medicine into respective acceptable and unacceptable groups.

19. The device as in claim 18, wherein said separating means comprises air discharge nozzles positioned relative to said second drum, said nozzles actuated by said determination logic to selectively remove pieces from said second drum and convey them into said respective groups.

20. The device as in claim 1 further comprising means to disengage said means for rotating said first and second drums when a driving load exceeds a predetermined value.

21. The device as in claim 20 wherein said means to disengage comprises a tortion spring having a tension limit substantially the same as said predetermined value, said tortion spring coupled to a driving pin whereby said driving pin is urged to a position of disengagement by said tortion spring when said predetermined value is exceeded.

22. The device as in claim 20 wherein said means to disengage comprises means to sense the angular speed of said first drum and electrical brake means responsive to said means to sense the angular speed to discontinue drum rotation.

* * * * *